(12) United States Patent
Saulenas et al.

(10) Patent No.: US 7,182,734 B2
(45) Date of Patent: Feb. 27, 2007

(54) RETRACTING NEEDLE SAFETY DEVICE

(75) Inventors: William Saulenas, Wayne, NJ (US); Michelle V. Sullivan, Wayne, NJ (US); Bradley Wilkinson, North Haledon, NJ (US); Kirk D. Swenson, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/215,386

(22) Filed: Aug. 8, 2002

(65) Prior Publication Data

US 2003/0040717 A1 Feb. 27, 2003

Related U.S. Application Data

(60) Provisional application No. 60/311,006, filed on Aug. 9, 2001.

(51) Int. Cl.
*A61B 5/00* (2006.01)

(52) U.S. Cl. ...................................... 600/573; 604/110

(58) Field of Classification Search ................ 604/110, 604/181, 187, 192, 194, 195–198; 128/919; 600/573
See application file for complete search history.

(56) References Cited

U.S. PATENT DOCUMENTS

| | | | |
|---|---|---|---|
| 4,592,744 A | 6/1986 | Jagger et al. ............. 604/192 |
| 4,731,059 A | 3/1988 | Wanderer et al. ........... 604/192 |
| 4,747,831 A | 5/1988 | Kulli ......................... 604/110 |
| 4,838,869 A | 6/1989 | Allard ........................ 604/195 |
| 4,846,808 A | 7/1989 | Haber et al. ............... 604/195 |
| 4,871,355 A | 10/1989 | Kikkawa ..................... 604/198 |
| 4,900,307 A | 2/1990 | Kulli ......................... 604/110 |
| 4,908,022 A | 3/1990 | Haber |
| 4,917,673 A | 4/1990 | Coplin ....................... 604/198 |
| 4,927,414 A | 5/1990 | Kulli ......................... 604/110 |
| 4,942,881 A | 7/1990 | Al-Sioufi et al. ........... 128/763 |
| 4,991,601 A | 2/1991 | Kasai et al. ................ 128/763 |
| 4,993,426 A | 2/1991 | Spencer ..................... 128/763 |
| 4,994,034 A | 2/1991 | Botich et al. ............... 604/110 |
| 5,030,209 A | 7/1991 | Wanderer et al. ........... 604/198 |
| 5,062,837 A | 11/1991 | Al-Sioufi et al. ........... 604/240 |
| 5,069,225 A | 12/1991 | Okamura .................... 128/765 |
| 5,120,311 A | 6/1992 | Sagstetter et al. .......... 604/110 |
| 5,143,083 A | 9/1992 | Al-Sioufi et al. ........... 128/763 |

(Continued)

FOREIGN PATENT DOCUMENTS

WO  WO 90/02515  3/1990

(Continued)

*Primary Examiner*—LoAn H. Thanh
(74) *Attorney, Agent, or Firm*—Mark J. Schildkraut

(57) ABSTRACT

A retractable safety needle assembly is provided. The needle assembly includes a tubular outer body, a retraction assembly contained with the outer body and a biasing element for applying a retraction force therebetween. The retraction assembly includes a cannula having an intravenous puncture tip and a non-patient puncture tip at opposing ends. In a first position, the intravenous puncture tip extends from a first end of the tubular outer body. The retraction assembly is adapted for movement within the tubular outer body from the first position to a second position in which the intravenous puncture tip and the non-patient puncture tip are contained entirely within the tubular outer body and are offset from a general axis defining the outer body.

24 Claims, 17 Drawing Sheets

U.S. PATENT DOCUMENTS

| | | | |
|---|---|---|---|
| 5,188,599 A | 2/1993 | Botich et al. | 604/110 |
| 5,217,025 A | 6/1993 | Okamura | 128/765 |
| 5,219,333 A | 6/1993 | Sagstetter et al. | 604/110 |
| 5,407,431 A | 4/1995 | Botich et al. | 604/110 |
| 5,591,138 A | 1/1997 | Vaillancourt | 604/263 |
| 5,616,136 A | 4/1997 | Shillington et al. | 604/240 |
| 5,637,101 A | 6/1997 | Shillington | 604/242 |
| 5,685,863 A | 11/1997 | Botich et al. | 604/198 |
| 5,693,028 A | 12/1997 | Shillington | 604/240 |
| 5,755,673 A | 5/1998 | Kinsey | 600/577 |
| 5,788,677 A | 8/1998 | Botich et al. | 604/195 |
| 5,797,490 A | 8/1998 | Fujii et al. | 206/365 |
| 5,800,395 A | 9/1998 | Botich et al. | 604/110 |
| 5,810,775 A | 9/1998 | Shaw | 604/110 |
| 6,004,278 A | 12/1999 | Botich et al. | 600/576 |
| 6,024,727 A | 2/2000 | Thorne et al. | 604/195 |
| 6,039,713 A | 3/2000 | Botich et al. | 604/110 |
| 6,074,373 A | 6/2000 | Sudo et al. | 604/241 |
| 6,077,244 A | 6/2000 | Botich et al. | 604/110 |
| 6,096,005 A | 8/2000 | Botich et al. | 604/110 |
| 6,123,688 A | 9/2000 | Botich et al. | 604/220 |
| 6,179,812 B1 | 1/2001 | Botich et al. | 604/110 |
| 6,302,868 B1 | 10/2001 | Mohammad | 604/192 |
| 6,524,276 B1 * | 2/2003 | Halseth et al. | 604/110 |
| 2002/0004648 A1 | 1/2002 | Larsen et al. | 604/195 |

FOREIGN PATENT DOCUMENTS

| | | |
|---|---|---|
| WO | 9923947 | 5/1999 |
| WO | 9944660 | 9/1999 |
| WO | 9947194 | 9/1999 |
| WO | 0006221 | 2/2000 |
| WO | 0012160 | 3/2000 |
| WO | 0027450 | 5/2000 |
| WO | 0035367 | 6/2000 |
| WO | 0137898 | 5/2001 |
| WO | 0145776 | 6/2001 |
| WO | 0166179 | 9/2001 |
| WO | 0178595 | 10/2001 |
| WO | 0193924 | 12/2001 |

* cited by examiner

RETRACTING NEEDLE SAFETY DEVICE

CROSS-REFERENCE TO RELATED APPLICATION

This application claims the benefit of earlier filed U.S. Provisional Patent Application Ser. No. 60/311,006 filed Aug. 9, 2001, entitled "Retracting Needle Safety Device".

BACKGROUND OF THE INVENTION

1. Field of the Invention

The present invention relates to a needle assembly having safety elements for safe and convenient handling. More particularly, the present invention relates to a needle assembly having a double-ended needle for collecting or delivering fluid samples from or into a patient and which includes a retracting assembly for retraction of the needle.

2. Description of Related Art

Disposable medical devices having piercing elements are typically used for administering a medication or withdrawing a fluid, such as blood collecting needles, fluid handling needles and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after use.

A popular design configuration of previously available blood collection systems includes a double-ended needle assembly, an evacuated collection tube, and a holder for maintaining the needle assembly and the collection tube in fixed relation. The double-ended needle assembly, which is also referred to as a cannula, has a bore extending therethrough and a hub near a central region thereof. The evacuated fluid collection tube includes a puncturable stopper at one end thereof. In this type of blood collection system, the holder typically has a housing at one end thereof for receiving the needle assembly. Likewise, the holder also has a hollow body with an opening at an opposite end thereof for receiving the collection tube. The needle assembly is rigidly received within the housing of the holder such that a first end of the needle extends forwardly of the holder for puncturing a vein of a patient. The opposite, second end of the needle extends into the hollow body of the holder. Upon assembly of the blood collection system, the needle assembly is inserted into the housing and the collection tube is inserted through the open end of the hollow body until the second end of the needle pierces the puncturable stopper of the collection tube, thereby allowing fluid communication between the interior of the collection tube and the bore which extends through the needle assembly. To draw a blood specimen from a patient using one of these blood collection systems, the evacuated collection tube is partially inserted into one end of the holder, the first end of the needle is inserted into a patient's vein, and the collection tube is fully inserted into the holder such that blood will be drawn through the bore of the needle assembly and into the fluid collection tube. After drawing the specimen, the collection tube is removed so that the blood contained therein can be analyzed and the needle assembly is detached for disposal.

In addition to being capable of accommodating blood collection tubes, the holders of some fluid transfer systems are compatible with fluid containers having a fluid to be injected into a patient. Thus, such holders can be used to inject fluid into, as well as draw blood specimens from, a patient.

In order to reduce the risk of incurring an accidental needle-stick wound, protection of the used needle tip becomes important. With concern about infection and transmission of diseases, methods and devices to enclose the used disposable needle have become very important and in great demand. Many arrangements have been designed for protecting used needle tips involving retracting the needle within a housing. For example, U.S. Pat. No. 5,810,775 to Shaw discloses a collection assembly which provides for retraction of the intravenous needle at the patient end of the assembly, and further discloses a hinged cap at the open end of the housing of the holder. After drawing a specimen into a collection tube, the collection tube is removed, and the hinged cap is closed over the opening of the holder, thereby activating the needle retraction and blocking access to the second end of the needle at the non-patient end. Activation of the hinged cap and the retraction mechanism requires substantial manipulation by the user and cannot be conveniently accomplished with a single hand, as is ideal for typical phlebotomy practice.

U.S. Pat. No. 4,846,808 to Haber et al. discloses a safety syringe including a needle, which can be manually retracted by sliding an inner needle carrier within an outer housing. The needle carrier includes a portion which can be pivoted to rotate and bend the needle to a canted and bent position toward the outside sleeve. Such an assembly requires multiple movements of the needle carrier by the operator to retract and to pivot and bend the needle, and does not provide effective protection at the non-patient tip of the needle within the housing.

Accordingly, a need exists for a needle assembly which provides effective protection from both ends of a double-ended needle with simple and efficient retraction of the needle, and which is simple to manufacture and easy to operate.

SUMMARY OF THE INVENTION

The present invention is directed to a retractable safety needle assembly, which includes a generally tubular outer body and a retraction assembly positioned within the outer body. The outer body includes a first end, a second end, and a tubular wall extending along an axis from the first end to the second end, defining an interior opening therein. The outer body further includes a guide channel, at least a portion of which is offset from the axis. The retraction assembly is positioned within the interior of the opening of the outer body. The retraction assembly includes a cannula having an intravenous puncture tip and a non-patient puncture tip, and includes a fin for corresponding engagement with the guide channel of the outer body. The retraction assembly is adapted for movement within the interior opening of the outer body from a first position in which the intravenous puncture tip extends from the first end of the outer body to a second position in which the intravenous puncture tip and the non-patient puncture tip are contained entirely within the outer body and the cannula is offset from the axis of the outer body. The needle assembly further includes a retaining element for preventing movement of the retraction assembly between the first position and the second position, as well as a biasing element for applying a retraction force between the retraction assembly and the outer body assembly to move the retraction assembly from the first position to the second position upon release of the means for preventing movement.

Desirably, the outer body includes a pair of guide channels on opposing sides of the wall and the retraction assembly includes a pair of fins for respective corresponding engagement with the pair of guide channels. The pair of guide channels may extend along opposing sides of the wall, and slope downwardly toward the second end of the outer body.

The wall of the outer body may include a recess extending within the interior opening of the outer body, which is adapted for accommodating the non-patient puncture tip when the retraction assembly is in the second position.

Moreover, the outer body may include an opening extending through the wall, with the retraction assembly including a tab which extends through the opening of the wall. Such a tab provides for interference engagement with the wall at the opening, thereby establishing a retaining element for preventing movement of the retraction assembly. The outer body may further include an insert sleeve which extends within the second end into the interior opening thereof, with the insert sleeve including a channel which is adapted for corresponding engagement with the tab when the retraction assembly is moved to the second position.

The retraction assembly may be irreversibly movable from the first position to the second position. The assembly may further include a lock mechanism for locking the retraction assembly in the second position. Desirably, the guide channel includes a notch, with the notch acting as a lock for preventing the fin from moving within the guide channel and thereby preventing the retraction assembly from moving from the second position to the first position.

A lock mechanism may also be provided by including at least one, and preferably two fin fingers extending from each fin, and by including at least one and preferably two corresponding notches within each guide channel. The fin fingers and the corresponding notches can be moved to a position of interference engagement when the retraction assembly is in the second position, thereby acting as a locking mechanism to prevent the retraction assembly from moving from the second position back to the first position. The guide channel may also include a stop extending from an interior surface of the wall within the guide channel, with the stop desirably including a forward ramped surface and a rearward shoulder. The forward ramped surface causes the fin to radially flex when the fin contacts the stop during movement of the retraction assembly from the first position to the second position, and the shoulder provides for interference engagement with the fin when the retraction assembly is in the second position to prevent the fin from moving within the guide channel, thereby preventing the retraction assembly from moving from the second position to the first position.

The guide channel may also include a recess extending within the wall of the outer body at a rearward portion of the guide channel, with the fin adapted for radial outward flexing for engagement with the recess when the retraction assembly is in the second position, thereby preventing the fin from moving within the guide channel and preventing the retraction assembly from moving from the second position to the first position.

DETAILED DESCRIPTION

Figure 1:
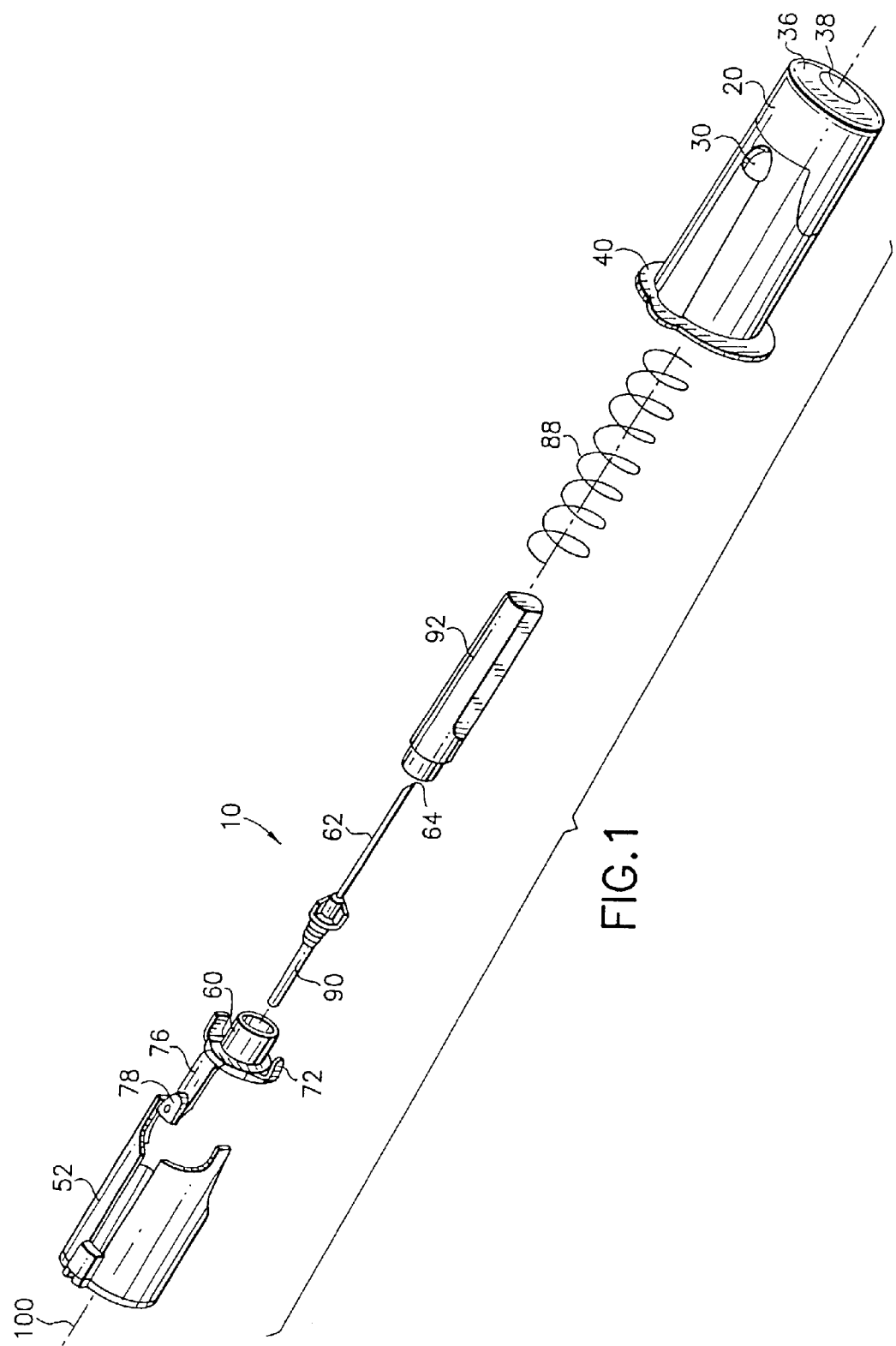
FIG. 1 is an exploded perspective view of a retracting safety needle assembly in accordance with the present invention.
Figure 2:
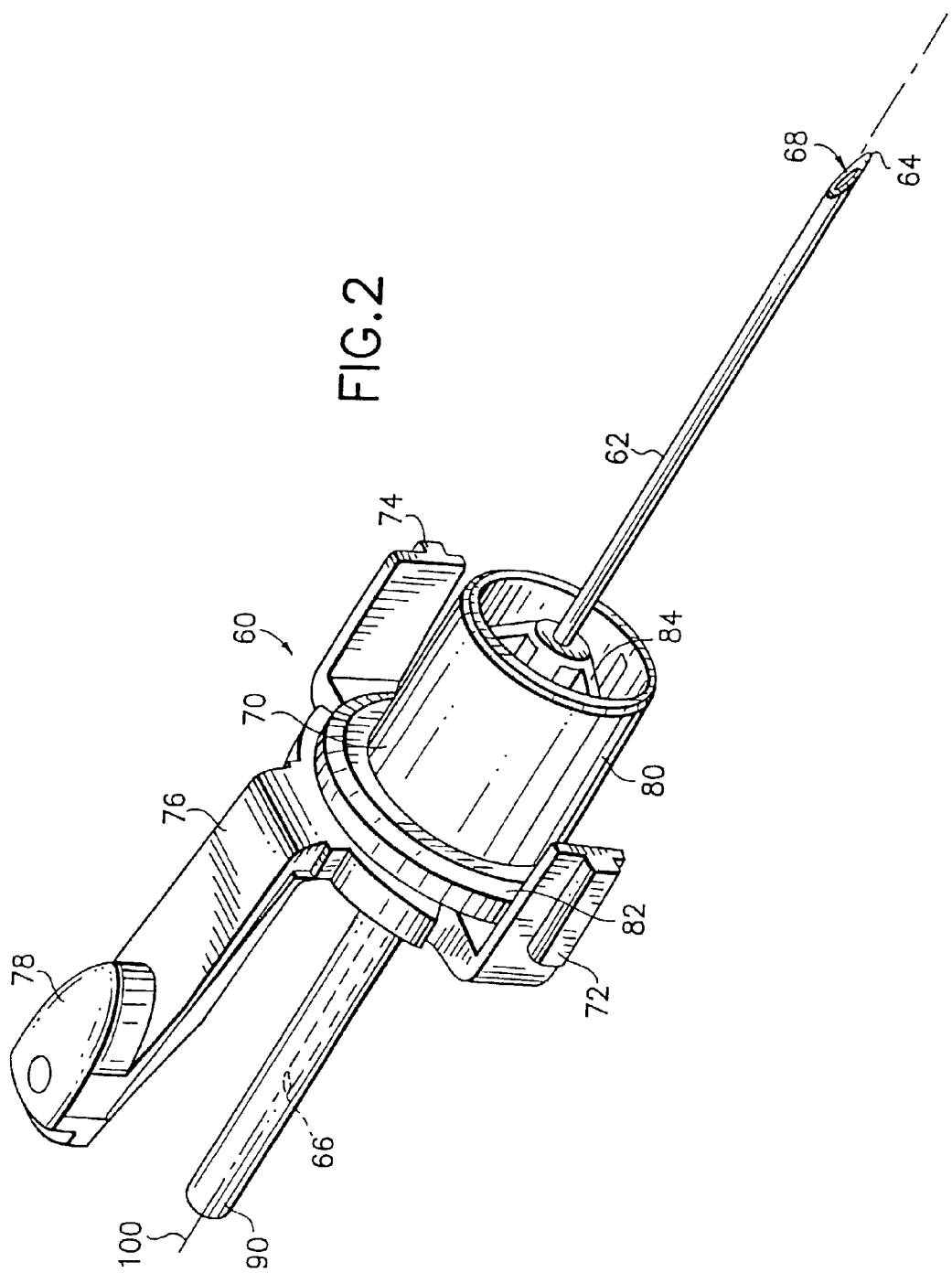
FIG. 2 is a perspective view of the retraction assembly of the retracting safety needle assembly of FIG. 1.

While the present invention is satisfied by embodiments in many different forms, there is shown in the drawings and will herein be described in detail, the preferred embodiments of the invention, with the understanding that the present disclosure is to be considered as examplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The present invention is generally directed to a retracting safety needle assembly, which allows for safe and convenient retraction of a phlebotomy needle, such as a double-ended needle, into a holder device. Generally speaking, retraction of the needle is accomplished by activating a button on the assembly, which enables a spring member to force a needle retraction assembly into the general cavity or interior opening of the holder. After activation, the device is safe from accidental needle sticks, which may occur during disposal of a needle in a conventional container.

Referring to the drawings in which like reference characters refer to like parts throughout the several views thereof, FIGS. 1–8 illustrate a retracting safety needle assembly in accordance with the present invention and the related features. The safety needle assembly includes a needle assembly in the form of a double-ended needle in combination with a needle holder for collecting blood samples.

Needle assembly 10 of the present invention is shown generally in FIGS. 1–8. Needle assembly 10 includes a holder 12, which is adapted for use in connection with a needle retraction assembly 60.

Holder 12, is defined generally by hollow tubular outer body 20, which includes first end 22, second end 24, and tubular wall 26 extending therebetween along an axis 100 which generally defines the elongated shape of holder 12. Outer body 20 further includes flange 40 at second end 24. First end 22 of holder 12 includes an opening 38 extending therethrough, while second end 24 is generally open-ended through opening 42, providing holder 12 as a generally hollow tubular outer body 20 having an interior opening 28 extending therethrough. Such interior opening 28 accommodates a blood sampling tube (not shown) during a sampling procedure, as is known in the art.

Figure 7:
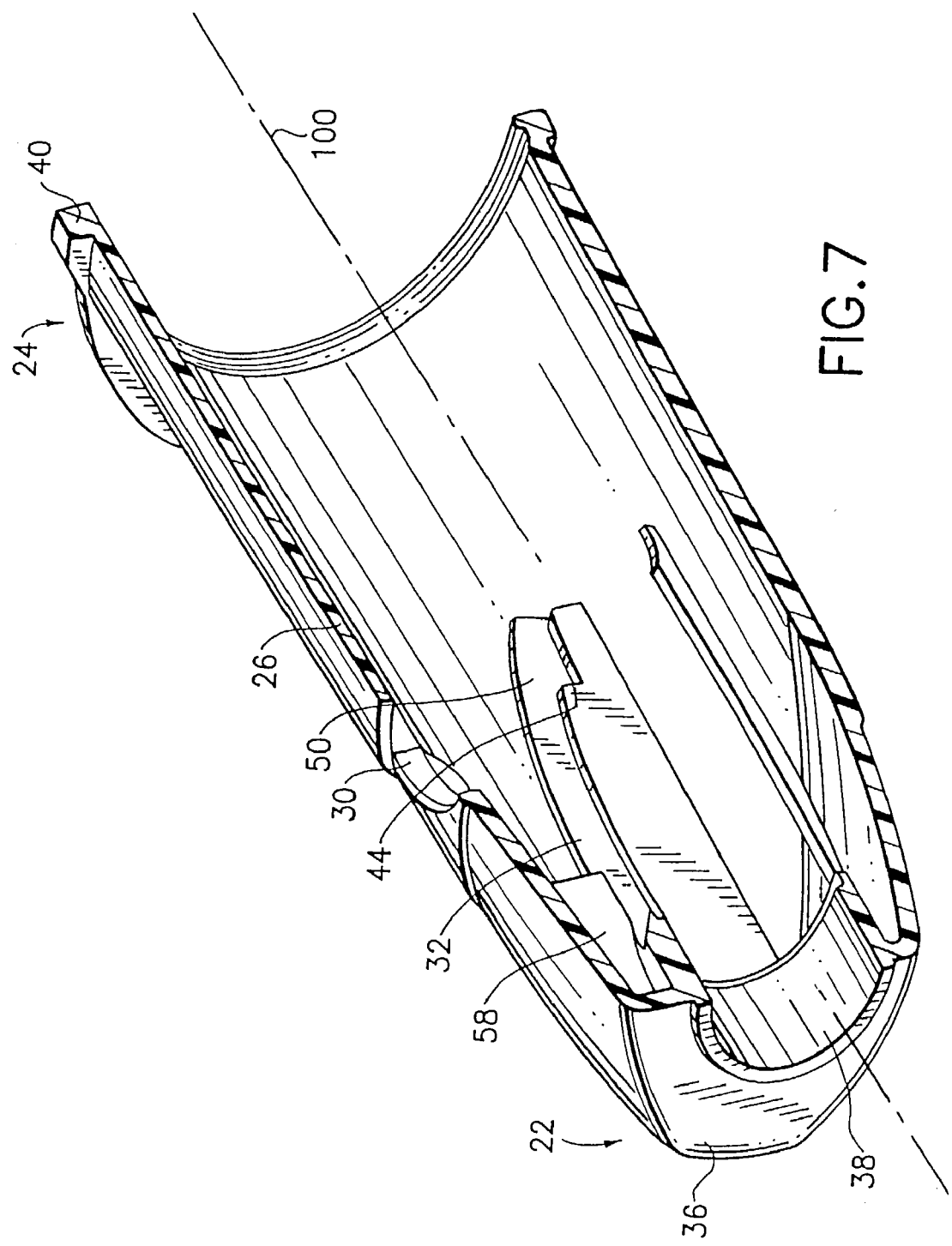
FIG. 7 is a perspective sectional view of the outer body of FIG. 6.
Figure 8:
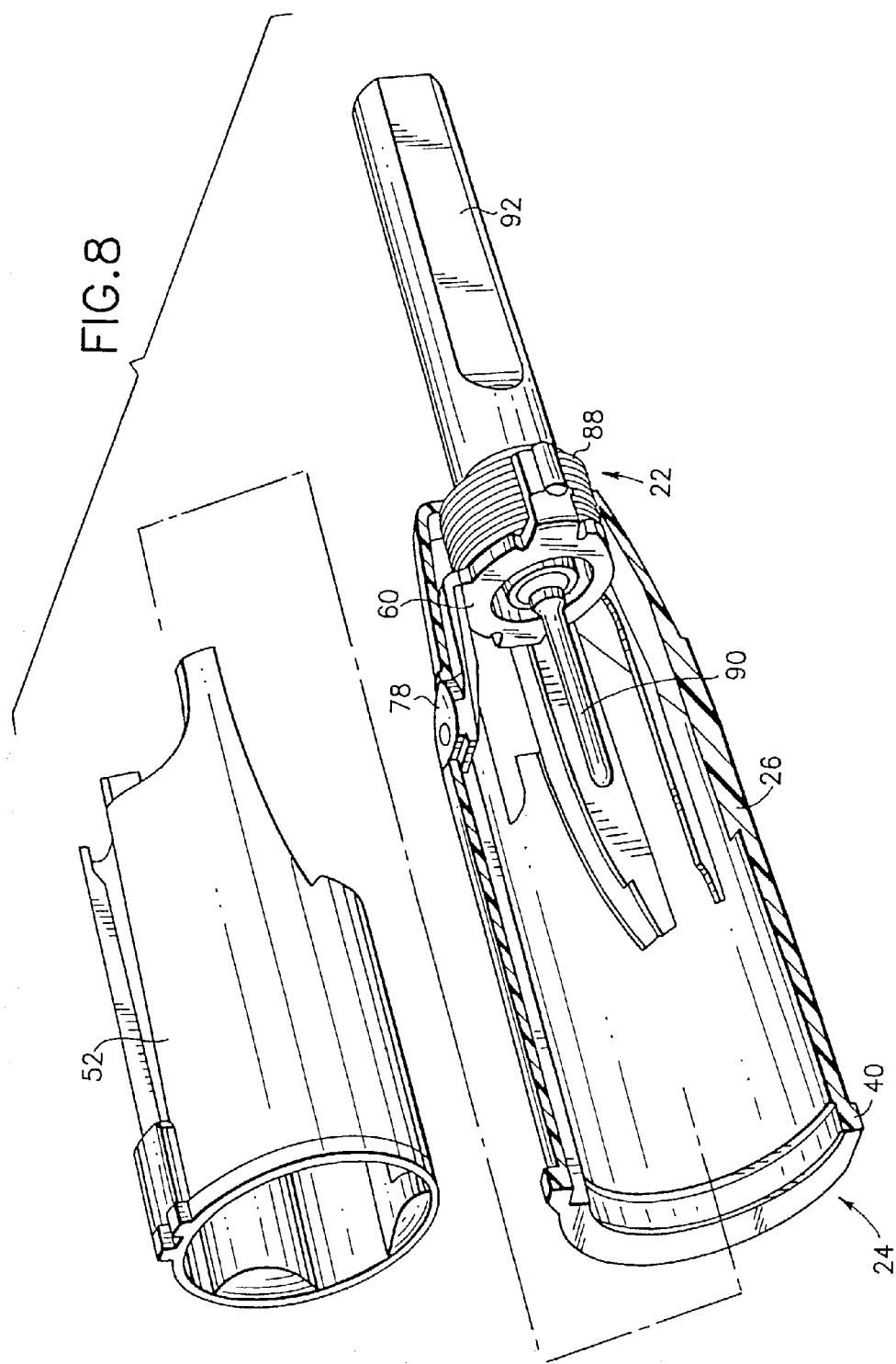
FIG. 8 is a perspective partial sectional view of the safety needle assembly of the present invention shown with the insert sleeve removed.

Outer body 20 of holder 12 includes a guide channel, desirably a pair of guide channels 32 and 34 extending along the interior surface of tubular wall 26 within interior opening 28. Guide channels 32 and 34 provide for corresponding engagement between holder 12 and retraction assembly 60, as will be discussed in more detail herein. Guide channels 32 and 34 are desirably provided on opposing sides of tubular wall 26. Desirably, guide channels 32 and 34 are provided on opposing sides of tubular wall 26 at a position adjacent to or in a plane with axis 100, and extend along the interior surface of tubular wall 26 in a manner offset from axis 100. For example, as seen in FIG. 7, guide channel 32 extends along the interior surface of tubular wall 26 in a rearward direction from first end 22 to second end 24 of outer body 20, and slopes in a downward direction toward second end 24, in a direction offset from axis 100. Generally speaking, guide channels As will be described in more detail herein, such extension in a direction offset from axis 100 provides for retracted movement of the retraction assembly 60 in an offset or canted manner within holder 12.

Holder 12 may be comprised of moldable parts which can be mass produced from a variety of materials including, for example, polyethylene, polyvinyl chloride, polystyrene or the like. As such, it may be desirable to provide holder 12 as two separate members, for example, outer body 20 and insert sleeve 52, to assist in molding procedures. Insert sleeve 52 provides holder 12 with structural elements which may be difficult to achieve if holder 12 were molded in one piece. For example, guide channels 32 and 34 may be difficult to mold within holder 12, however by providing insert sleeve 52 within holder 12, the wall of insert sleeve 52 can act as an edge of guide channels 32 and 34. Desirably, holder 12 includes outer body 20 with insert sleeve 52 fixedly attached and extending through opening 42 at second end 24 of outer body 20. Such attachment may be accomplished, for example, through the use of a medical grade adhesive. Insert sleeve 52 extends within interior opening 28 of outer body 20 and includes an outer diameter which is substantially the same as the internal diameter of outer body 20, such that insert sleeve 52 fits snugly within and against the internal surface of tubular wall 26.

As noted, needle assembly 10 further includes retraction assembly 60. Retraction assembly 60 is positioned within interior opening 28 of outer body 20. Generally speaking, retraction assembly 60 includes a cannula 62 having a first end with an intravenous puncture tip 64, and a second end with a non-patient puncture tip 66. A central bore or lumen 68 extends through cannula 62 from intravenous puncture tip 64 to non-patient puncture tip 66, providing for the passage of fluid therethrough. Intravenous puncture tip 64 is provided for insertion into the vein of a patient, and non-patient puncture tip 66 is provided for puncturing of an evacuated tube, for example, during a blood collection procedure. Accordingly, intravenous puncture tip 64 is desirably shaped to provide for ease of insertion and minimal discomfort during venipuncture, such as with a tapered pointed end, as is shown in the Figures and is known in the art. Retraction assembly 60 may further include elastomeric sleeve 90 extending about non-patient puncture tip 66 of cannula 62, as is generally known in the art.

Retraction assembly 60 further includes body 70, which defines the general shape of retraction assembly 60, with cannula 62 extending through body 70. Cannula 62 may be integrally formed with body 70 to form retraction assembly 60, or, desirably, may be provided as a separate member, which is separately attached to body 70. Body 70 includes a hub 80, which provides for attachment between cannula 62 and body 70. Such attachment may be, for example, through a threaded or a snap-fit attachment, or through permanent bonding. In one embodiment, hub 80 may include internal threads and cannula 62 may include external threads for threaded engagement therebetween. As such, a standard conventional double-ended needle can be used as cannula 62 in conjunction with hub 80 to provide retraction assembly 60 for use with needle assembly 10 of the present invention.

Retraction assembly 60 is adapted for movement within interior opening 28 of holder 12, for retraction of cannula 62. As such, the outer diameter of body 70 of retraction assembly 60 is smaller than the internal diameter of outer body 20. Movement of retraction assembly 60 within outer body 20 may be effected through a respective corresponding relation or engagement between retraction assembly 60 and outer body 20. For example, fins 72 and 74 are provided on opposing sides of body 70, for corresponding engagement with guide channels 32 and 34 on the interior surface of tubular wall 26 of outer body 20. Fins 72 and 74 are shaped and configured to engage and ride within guide channels 32 and 34, respectively, during movement of retraction assembly 60.

Retraction assembly 60 is adapted for movement within interior opening 28 of outer body 20 of holder 12 from a first position in which intravenous puncture tip 64 extends from first end 22 of outer body 20 through opening 38 at front end wall 36, to a second position in which intravenous puncture tip 64 and non-patient puncture tip 66 are contained entirely within outer body 20 and cannula 62 is offset from axis 100 of outer body 20.

Figure 3:
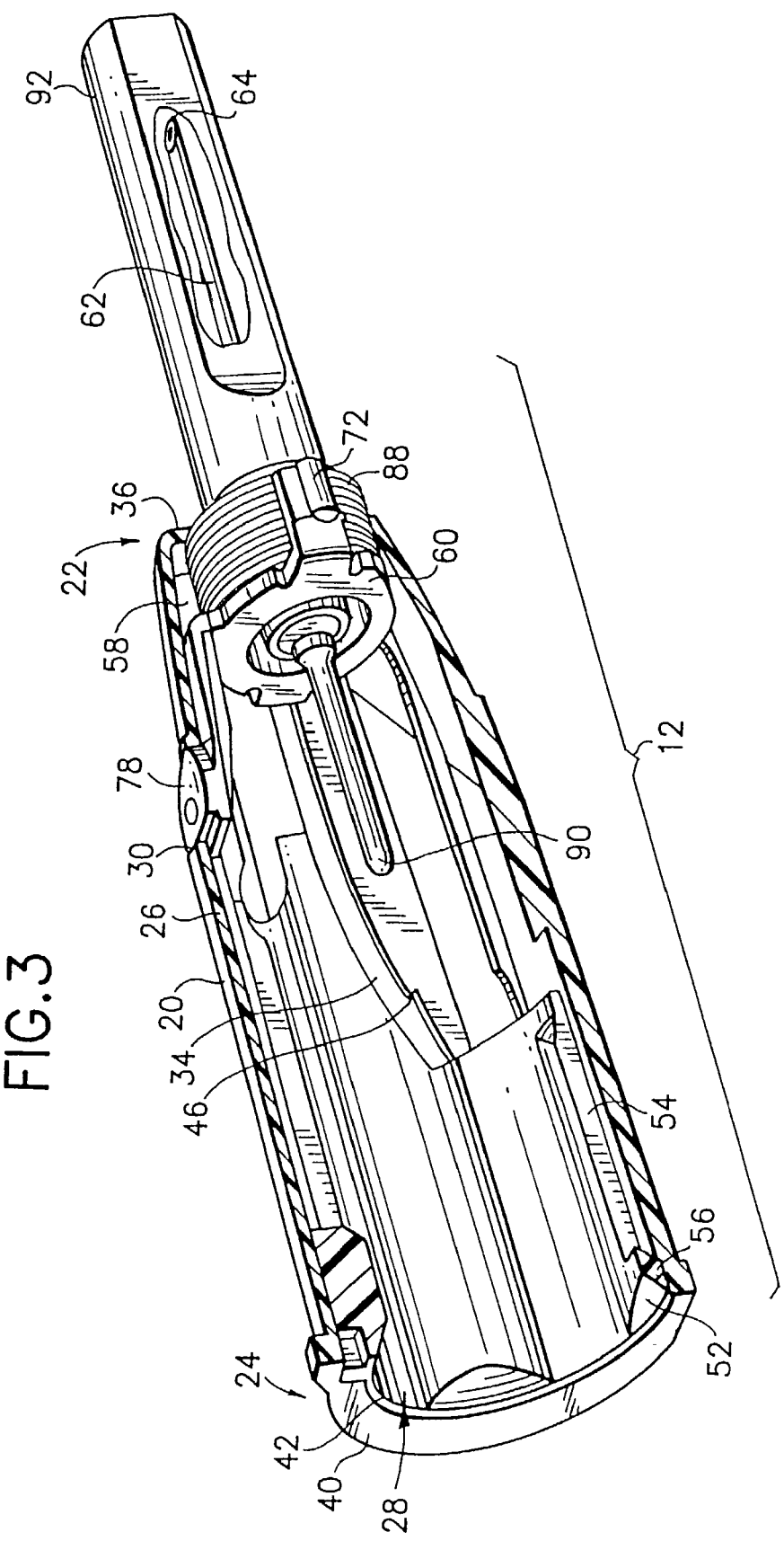
FIG. 3 is a perspective partial sectional view of the retracting safety needle assembly of the present invention shown in a position ready for sampling.
Figure 4:
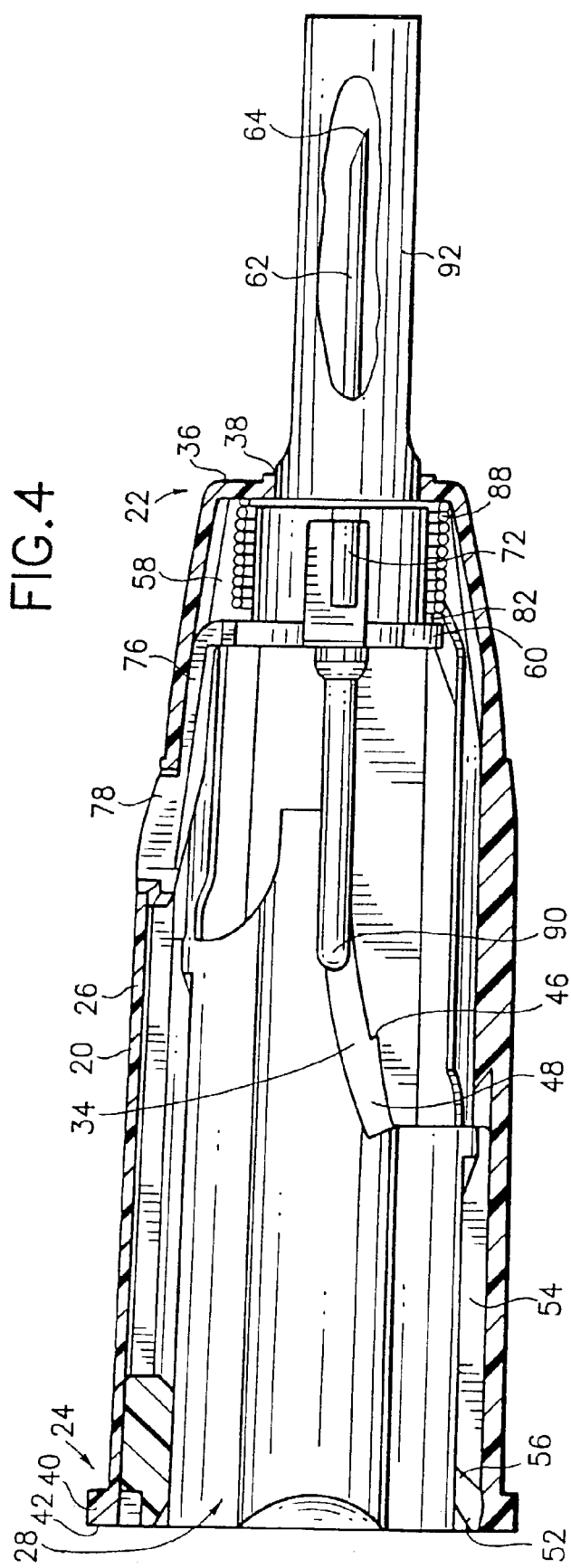
FIG. 4 is a cross-sectional view of the retracting safety needle assembly of FIG. 3 shown in a position ready for sampling.
Figure 5:
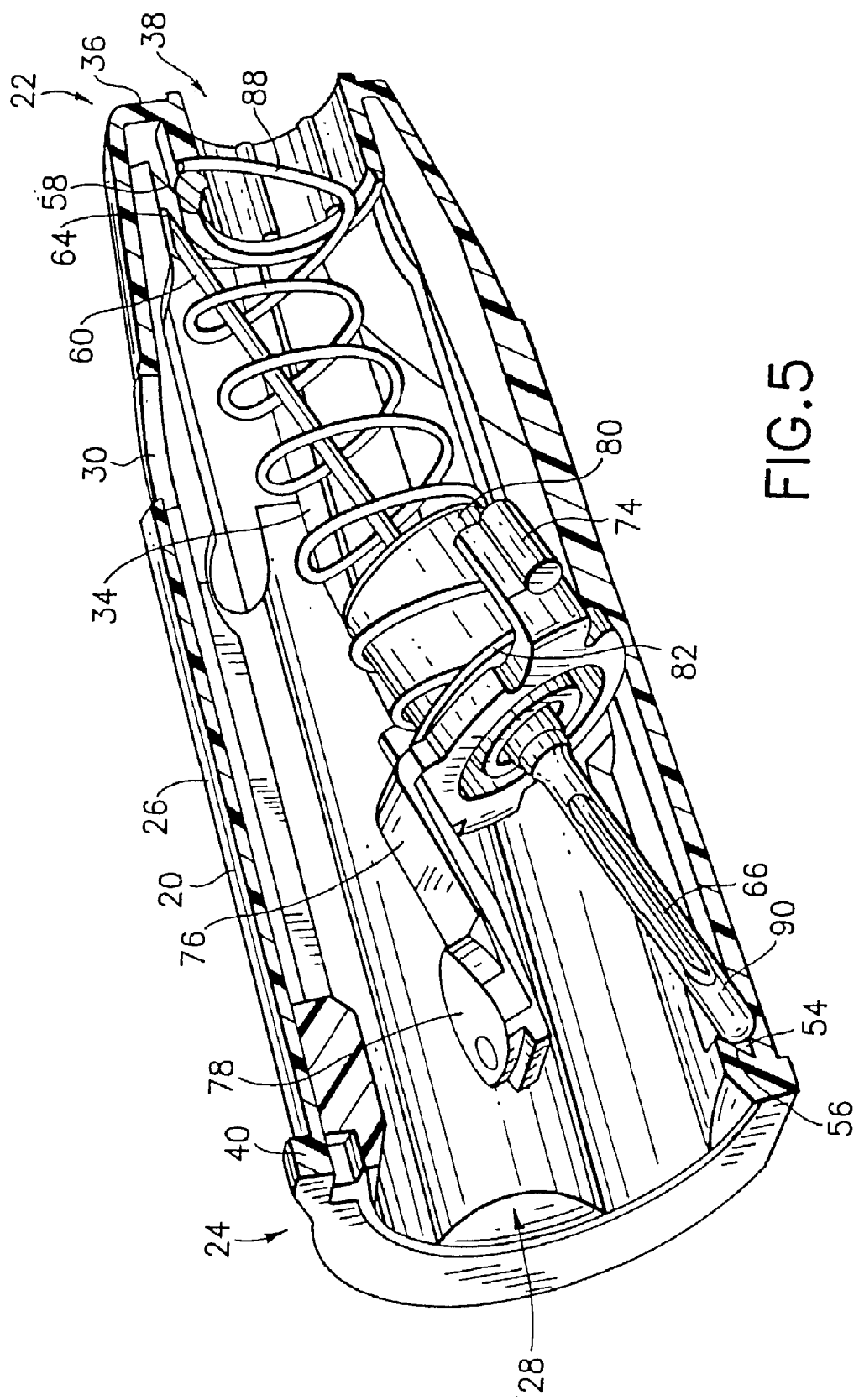
FIG. 5 is a perspective partial sectional view of the retracting safety needle assembly of FIG. 3 shown in a retracted position.
Figure 6:
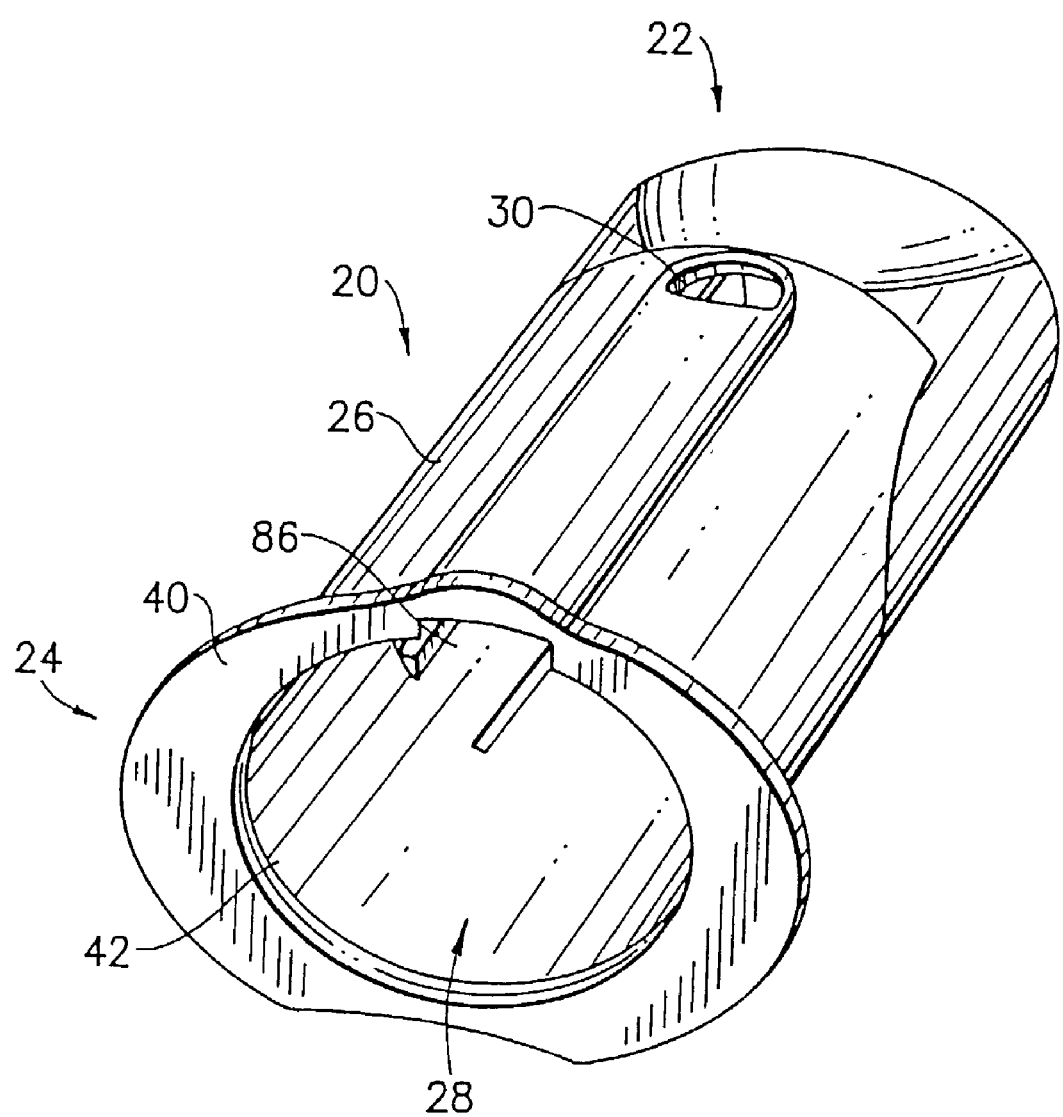
FIG. 6 is a perspective view of the outer body of the retracting safety needle assembly of FIG. 1.

More particularly, in a first position as shown in FIGS. 3–4, retraction assembly 60 is provided within interior opening 28 of outer body 20, with intravenous puncture tip 64 extending from first end 22 and with non-patient puncture tip 66 contained within interior opening 28 of outer body 20. Both intravenous puncture tip 64 and non-patient puncture tip 66 are generally in alignment with axis 100. In such a first position, needle assembly 10 is ready for sampling during a blood collection procedure, as will be discussed in more detail with respect to operation and use of the needle assembly 10. In the second position as shown in FIG. 5, retraction assembly 60 is retracted within outer body 20 of holder 12. In such a second position, cannula 62 is retracted entirely within outer body 20 of holder 12 such that intravenous puncture tip 64 is contained within interior opening 28 of outer body 20 behind front end wall 36, and non-patient puncture tip 66 is maintained within interior opening 28 of outer body 20 behind opening 42 at the second end 24 of outer body 20. The overall length of retraction assembly 60 from intravenous puncture tip 64 to non-patient puncture tip 66 should be less than the overall length of holder 12, such that cannula 62 fits entirely within interior opening 28 of outer body 20 in a canted position upon retraction of retraction assembly 60 within holder 12.

As noted, cannula 62 is offset from axis 100 when retraction assembly 60 is retracted to the second position. This is desirably achieved through the respective corresponding engagement between fins 72 and 74 of retraction assembly 60 and guide channels 32 and 34 of outer body 20. More particularly, as noted, guide channels 32 and 34 extend along the interior surface of tubular wall 26 in a direction offset from axis 100, such as by sloping downwardly toward second end 24. Such extension in a direction offset from axis 100 provides for retracted movement of the retraction assembly 60 in an offset or canted manner within holder 12. For example, fins 72 and 74 are guided along guide channels 32 and 34, respectively, and follow the sloping direction of guide channels 32 and 34. Since fins 72 and 74 are integral with body 70 of retraction assembly 60, body 70 follows the same movement in a sloping direction. Since cannula 62 is connected to body 70, cannula 62 also follows the same movement in a sloping direction. Thus, during movement to the second position, cannula 62 offsets from axis 100 such that non-patient puncture tip 66 and intravenous puncture tip 64 are no longer in alignment with axis 100.

While the invention is described with corresponding engagement between guide channels 32 and 34 within holder 12 and fins 72 and 74 extending from retraction assembly 60 for traveling in the guide channels 32 and 34, it is contemplated that such interrelating components can be switched, such that the retraction assembly includes guide channels and the holder includes fins extending within such guide channels. Moreover, it is contemplated that the guide channels may extend entirely through the wall of the holder.

Holder 12 may also include a pocket or recess 54 for accommodating non-patient puncture tip 66 when retraction assembly 60 is in the second position and is retracted within holder 12. Recess 54 may be provided as a channel extending along tubular wall 26 within interior opening 28. Desirably, recess 54 is established through the engagement between outer body 20 and insert sleeve 52, such as through a lip 56 extending from insert sleeve 52. Such a lip provides recess 54 as a pocket between lip 56 and the inner surface of tubular wall 26 extending to second end 24 of outer body 20. Recess 54 accommodates non-patient puncture tip 66 during and after retraction of retraction assembly 60 to the second position, by providing a channel against the interior surface of tubular wall 26. Recess 54 may further maintain non-patient puncture tip 66 in a safety position by maintaining non-patient puncture tip 66 against the wall surface within interior opening 28, and lip 56 may assist in holding non-patient puncture tip 66 in such a position.

In a similar manner, intravenous puncture tip 64 may be accommodated within a pocket 58 between front end wall 36 and tubular wall 26 of outer body 20 when retraction assembly 60 is in the second position and is retracted within holder 12. In such an embodiment, pocket 58 establishes a portion of the inner surface of tubular wall 26 at front end wall 36 for intravenous puncture tip 64 to rest upon when in such a second retracted position. Desirably, intravenous puncture tip 64 rests within interior opening 28 at a position adjacent pocket 58 when retraction assembly 60 is in the second position, as shown in FIG. 5. In this manner, any attempt to move retraction assembly 60 from the second position to the first position will cause intravenous puncture tip 64 to be guided into pocket 58 and against front end wall 36, since cannula 62 is offset from axis 100 when retraction assembly 60 is retracted to the second position. As such, retraction assembly 60 is prevented from moving in the reverse direction, i.e., from the second position to the first position.

Needle assembly 10 further includes a retaining element for preventing movement of retraction assembly 60 within outer body 20 of holder 12. For example, holder 12 may include an opening such as hole 30 extending through tubular wall 26 of outer body 20 into interior opening 28 for engagement with retraction assembly 60. Retraction assembly 60 may include a cantilevered arm 76 extending from an end of body 70, with tab 78 protruding from an end portion of arm 76. Arm 76 is provided for extension along needle assembly 10 within interior opening 28 of outer body 20, with tab 78 extending through hole 30 within tubular wall 26 of outer body 20. As best seen in FIGS. 3 and 4, tab 78 extends within hole 30 and abuts an edge of tubular wall 26 created by hole 30, providing for an interference engagement between tab 78 and tubular wall 26, thereby resisting and/or preventing movement of retraction assembly 60 within outer body 20.

Outer body 20 may further be provided with channel 86 extending from hole 30 along the inner surface of tubular wall 26 at a top portion thereof. Channel 86 is desirably formed as a groove in insert sleeve 52, and is established within outer body 20 through the interfitting relation between insert sleeve 52 and outer body 20. Tab 78 is adapted for slidable engagement within channel 86 when retraction assembly 60 is retracted.

Such interference engagement or restrictive movement may alternatively be accomplished by providing the holder and the retraction assembly with different cross-sectional shapes with respect to each other. For example, the holder may have an elliptical cross-sectional shape, while the retraction assembly has a circular cross-sectional shape. Interference engagement or restrictive movement is established due to the friction between such different shapes, thereby preventing movement of the retraction assembly within the outer body. Activation of such a needle assembly could be accomplished by squeezing the elliptical holder, thereby releasing the friction and the interference engagement between the holder and the retraction assembly.

Needle assembly 10 further includes means for storing energy, such as a biasing element for applying a force between retraction assembly 60 and holder 12. For example, compression spring 88 may be provided within holder 12 for exerting a biasing force between holder 12 and retraction assembly 60. As clearly seen in FIG. 4, compression spring 88 is provided between an inner surface of front end wall 36 of outer body 20 and shoulder 82 of body 70 of retraction assembly 60. Compression spring 88 is compressed when retraction assembly 60 is in the first position, and is partially or fully extended when retraction assembly 60 is in the second position. Compression spring 88 has stored energy when compressed, such as when retraction assembly 60 is maintained in the first position. Compression spring 88 may be constructed of any known material, and is desirably constructed of a material which is resistant to sterilization, such as stainless steel. While the present invention is described in terms of use of a compression spring 88, it is contemplated that other biasing elements or means of stored energy for providing a force between retraction assembly 60 and holder 12 are also contemplated, such as a tension spring or elastic strap which is capable of pulling retraction assembly 60 within holder 12, as opposed to pushing retraction assembly 60 within holder 12.

Preferably, retraction assembly 60 is irreversibly movable between the first position and the second position. More preferably, retraction assembly 60 is movable within holder 12 in only a single direction, from the first ready position to the second retracted position. As such, once retraction assembly 60 has been retracted within holder 12 from the first position to the second position, it cannot be reset to the first position, ready for sampling.

For example, tab 78 may be contained entirely within holder 12 upon retraction of retraction assembly 60 from the first position to the second position such that it no longer protrudes through hole 30, thus rendering movement of retraction assembly 60 by movement of tab 78 impossible. Also, needle assembly 10 may include structural features which prevent movement of retraction assembly 60 from the second position to the first position.

For example, as noted above, intravenous puncture tip 64 desirably rests within interior opening 28 at a position adjacent pocket 58 when retraction assembly 60 is in the second position, as shown in FIG. 5. Any attempt to move retraction assembly 60 from the second position to the first position will therefore cause intravenous puncture tip 64 to be guided into pocket 58 and against front end wall 36, thereby, preventing retraction assembly 60 from moving from the second position to the first position.

In addition, needle assembly 10 may be provided with a locking mechanism for preventing movement of retraction assembly 60 within holder 12 from the second position to the first position after retraction assembly 60 has been retracted within holder 12. For example, outer body 20 of holder 12 may include notches 44 and 46 within guide channels 32 and 34, respectively, forming notch pockets 48 and 50, respectively. Notches 44 and 46 are adapted to accommodate movement of fins 72 and 74 of retraction assembly 60 thereover upon movement of retraction assembly 60 from the first position to the second position. Also, notches 44 and 46 provide interference engagement with fins 72 and 74 after retraction assembly 60 is moved to the second position, preventing movement of fins 72 and 74 beyond notches 44 and 46 in the opposite direction, and thereby preventing movement of retraction assembly 60 to the first position.

As such, any movement of retraction assembly 60 from the second position to the first position is prevented. For example, if a force is applied to retraction assembly 60 in a forward axial direction of the offset axis of needle cannula 62 when retraction assembly 60 is in the second retracted position, intravenous puncture tip 64 will hit against front end wall 36 within pocket 58 and will be prevented from forward movement for re-exposure. Further, if a force is applied to retraction assembly 60 in an forward axial direction of axis 100 when in the second retracted position, fins 72 and 74 will be pushed against notches 44 and 46 thereby interfering and preventing forward movement and re-exposure.

Needle assembly 10 may further be provided with means for attachment of a needle cover 92, such as shoulder 84. Shoulder 84 is provided for engagement with needle cover 92, which covers intravenous puncture tip 64 of cannula 62 prior to use of needle assembly 10. Such a needle cover 92 may be constructed of rigid polymeric material, as is known in the art. Shoulder 84 preferably includes a profile to provide for a frictional engagement with the needle cover 92, such that the needle cover 92 is maintained in position about shoulder 84 in a friction fit, thereby covering and protecting cannula 62 until use.

Needle assembly 10 may also be provided with means for dampening the acceleration of retraction assembly 60 relative to holder 12, thereby preventing jerking of the retraction assembly and preventing splattering of fluid. For example, dampening agents such as greases, gels, gel resins, silicone oils or other medical grade viscous fluid can be applied directly to spring 88 and/or to the engagement surfaces of holder 12 and retraction assembly 60 such as the inner surface of front end wall 36 and shoulder 82.

Further, the profile of holder 12 may be designed so as to prevent it from rotating on a flat surface such as a patient's skin. For example, flange 40 may be provided with a flat edge on the bottom surface thereof, or may be provided with a concave rounded edge at the bottom surface, for matching the contour of a patient's arm.

Operation and use of the retracting safety needle assembly of the present invention will now be described. In use, needle assembly 10 is provided with retraction assembly 60 extending within holder 12, and with a portion of cannula 62 including intravenous puncture tip 64 extending from holder 12 through front opening 38, and with needle cover 92 extending over intravenous puncture tip 64.

Needle cover 92 extending over intravenous puncture tip 64 is removed. Venipuncture is then conducted in a known manner, whereby intravenous puncture tip 64 is then inserted into a vein of a patient. An evacuated tube having a piercable closure is then inserted into opening 42 of holder 12 and into interior opening 28, such that the piercable closure of the evacuated tube contacts sleeve 88 extending about non-patient puncture tip 66. When pressure is exerted on the evacuated tube, the piercable closure contacting sleeve 88 causes sleeve 88 to displace, thereby causing non-patient puncture tip 66 to puncture sleeve 88 and, in turn, the piercable closure of the evacuated tube. At such time, the interior of the evacuated tube and lumen 68 of cannula 62 are in fluid communication. Since the interior of the evacuated tube is at a negative pressure, blood is drawn from the vein of the patient, through lumen 68 of cannula 62 and into the evacuated tube. Multiple samples can be drawn into a number of successive evacuated tubes in this manner.

When all desired samples have been drawn, retraction of the needle assembly 10 is accomplished. Retraction of the needle assembly 10 may be accomplished while venipuncture is maintained, that is, while intravenous puncture tip 64 is maintained within the vein of the patient, in order to prevent an accidental needle stick prior to retraction of the needle. Retraction of the needle assembly 10 is accomplished by depressing tab 78 extending through hole 30. By depressing tab 78, tab 78 is forced through hole 30 of tubular wall 26 and into the interior opening 28 of holder 12. This releases the interference engagement between holder 12 and retraction assembly 60. Spring 88 is compressed, and therefore, exerts a biasing force between holder 12 and retraction assembly 60. By releasing the interference engagement between holder 12 and retraction assembly 60, the biasing force therebetween from spring 88 forces shoulder 82 of retraction assembly 60 and front end wall 36 of holder 12 apart, thereby forcing retraction assembly 60 to move within interior opening 28 of holder 12 in a direction away from first end 22 and toward second end 24.

Since cannula 62 is in fixed relation to retraction assembly 60, movement of retraction assembly 60 within holder 12 causes cannula 62 to move with respect to holder 12, such that intravenous puncture tip 64 moves through opening 38 and into interior opening 28 within holder 12. Moreover, since the overall length of cannula 62 is shorter than holder 12, non-patient puncture tip 66 is maintained within interior opening 28 of holder 12 even after intravenous puncture tip 64 retracts into interior opening 28.

With fins 72 and 74 of retraction assembly 60 extending within guide channels 32 and 34 of outer body 20, retraction assembly 60 is guided along the interior surface of outer body 20 of holder 12 in a direction toward second end 24 of holder 12 during movement within holder 12. Also, since guide channels 32 and 34 are offset from axis 100 and sloped downwardly toward second end 24 of holder 12, fins 72 and 74 follow such downward slope during movement. As such, retraction assembly 60 is offset from axis 100 during retraction thereof such that intravenous puncture tip 64 and non-patient puncture tip 66 are offset and angled toward tubular wall 26 of holder 12.

Further, upon movement of retraction assembly 60 within holder 12, non-patient puncture tip 66 displaces and rests within recess 54. Similarly, intravenous puncture tip 64 displaces after passing through front opening 38, and rests at a position adjacent pocket 58.

During movement of retraction assembly 60 within holder 12, fins 72 and 74 slide along guide channels 32 and 34 and pass over notches 44 and 46 and into notch pockets 48 and 50. The shape and design of notches 44 and 46 prevent fins 72 and 74 from reversing over notches 44 and 46 in the opposite direction, thereby locking retraction assembly 60 in the retracted position within holder 12. Moreover, any forcing of retraction assembly 60 within holder 12 in such an opposite direction would force intravenous puncture tip 64 against the inner surface of front end wall 36 within pocket 58, thereby further locking retraction assembly 60 in the retracted position within holder 12.

As such, intravenous puncture tip 64 and non-patient puncture tip 66 are effectively retracted within holder 12, and rendered inaccessible. Needle assembly 10 can then be appropriately discarded.

FIGS. 9–17 depict further embodiments of the present invention, and include many components which are substantially identical to the components of FIGS. 1–8. Accordingly, similar components performing similar functions will be numbered identically to those components of FIGS. 1–8, except that a suffix "a" will be used to identify those similar components in FIGS. 9–11, a suffix "b" will be used to identify those similar components in FIGS. 12 and 13, a suffix "c" will be used to identify those similar components in FIGS. 14–16, and a suffix "d" will be used to identify those similar components in FIG. 17.

It is noted that the orientation of FIGS. 9–17 showing alternate embodiments of the invention depict only a single fin of the retraction assembly, and further depict only a single guide channel within the outer body. It is to be understood, however, that the corresponding guiding relationship between the fins and the guide channels in the alternate embodiments of FIGS. 9–17 work in a similar manner as that discussed with respect to FIGS. 1–8, with the exception that the locking mechanism for retaining the assembly in the retracted position may vary between the different embodiments. As such, FIGS. 9–17 may depict a single fin on one side of the assembly and a guide channel on the opposing side of the assembly merely to demonstrate the relationship between the structures, with the understanding that similar features of the fin and guide channel may be provided to opposing sides of the assembly which are not shown.

Figure 9:
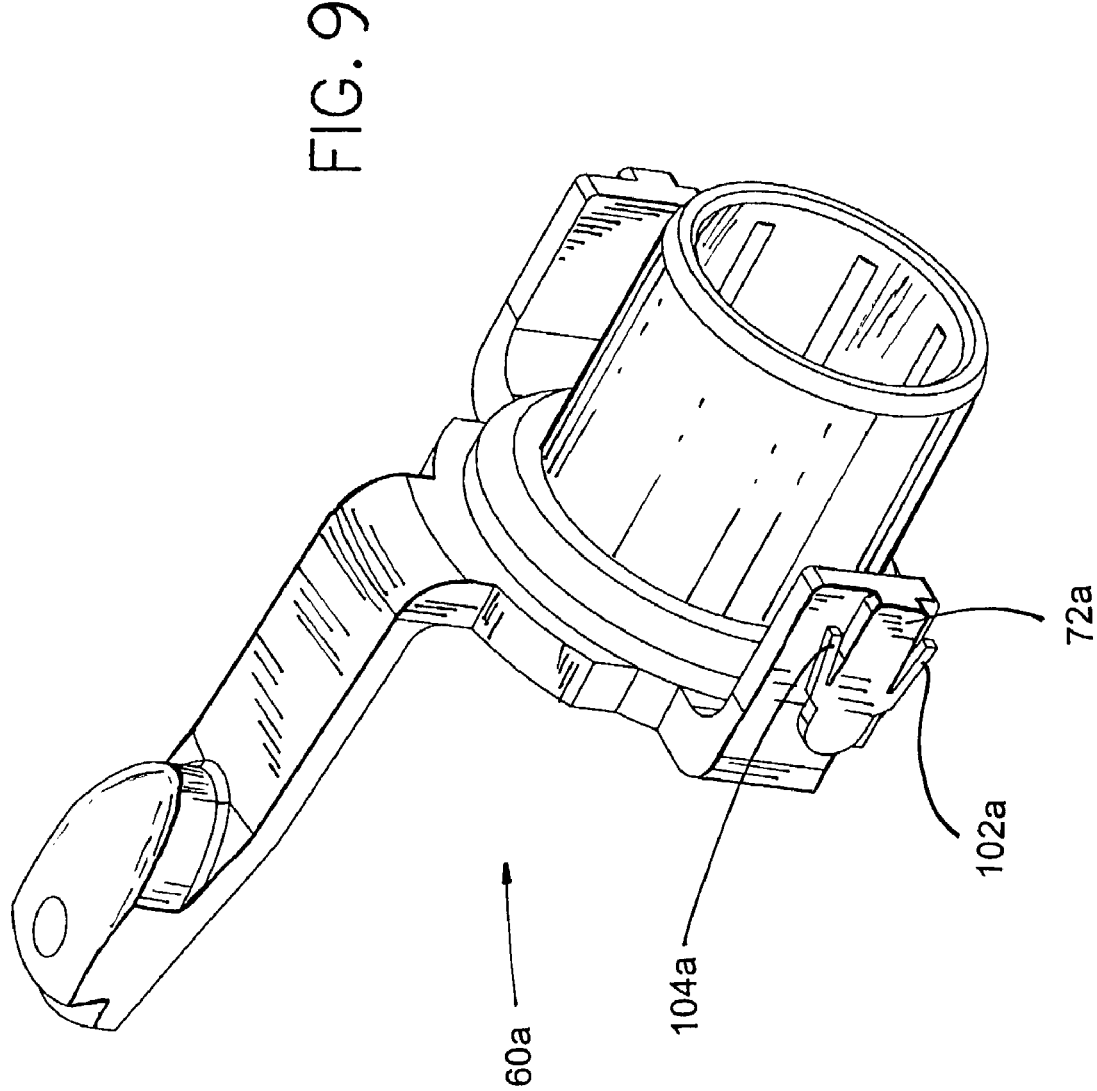
FIG. 9 is a perspective view of a retraction assembly in an alternate embodiment of the present invention.
Figure 10:
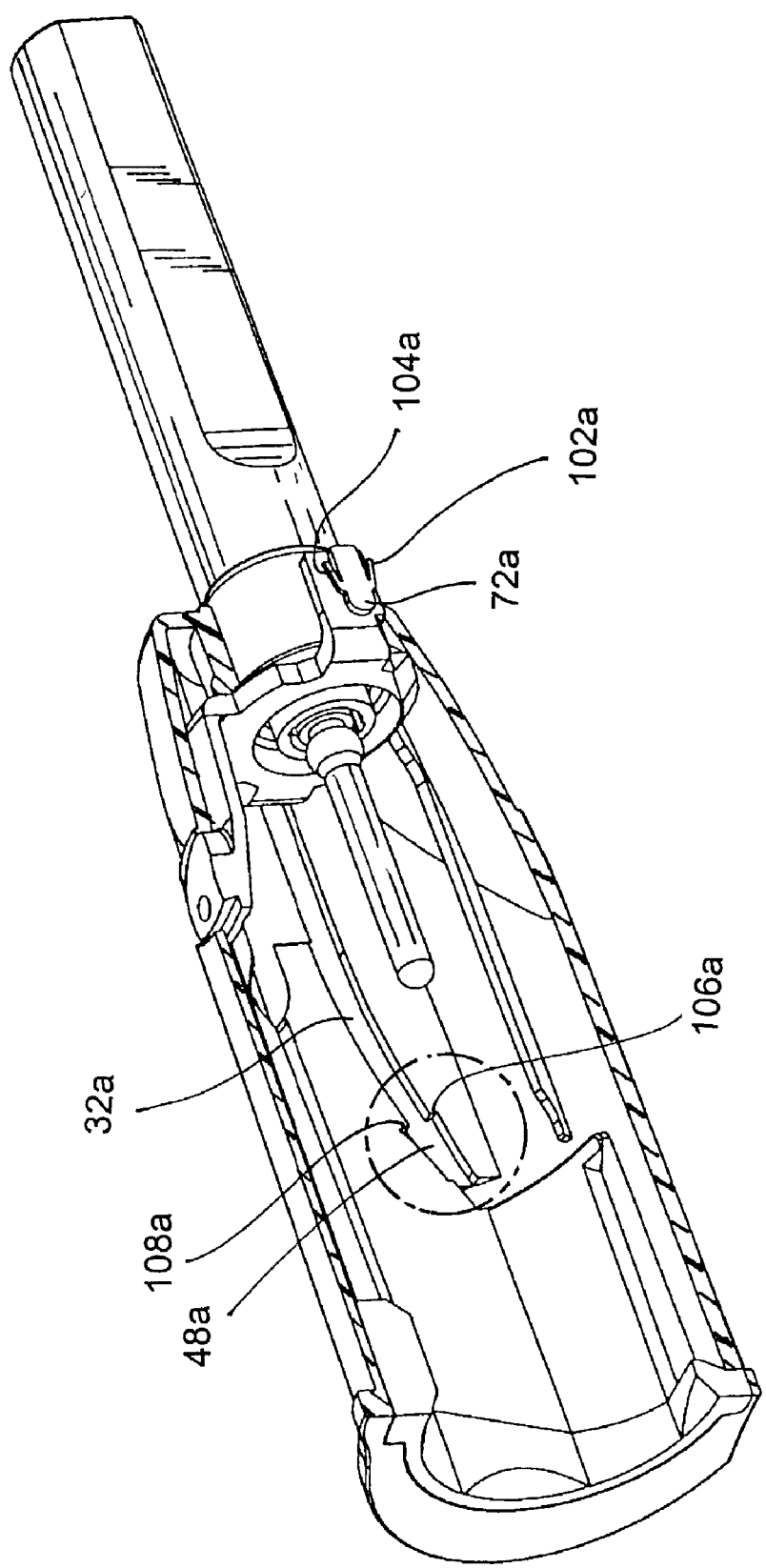
FIG. 10 is a perspective partial sectional view of a safety needle assembly in an alternate embodiment including the retraction assembly shown in FIG. 9.
Figure 11:
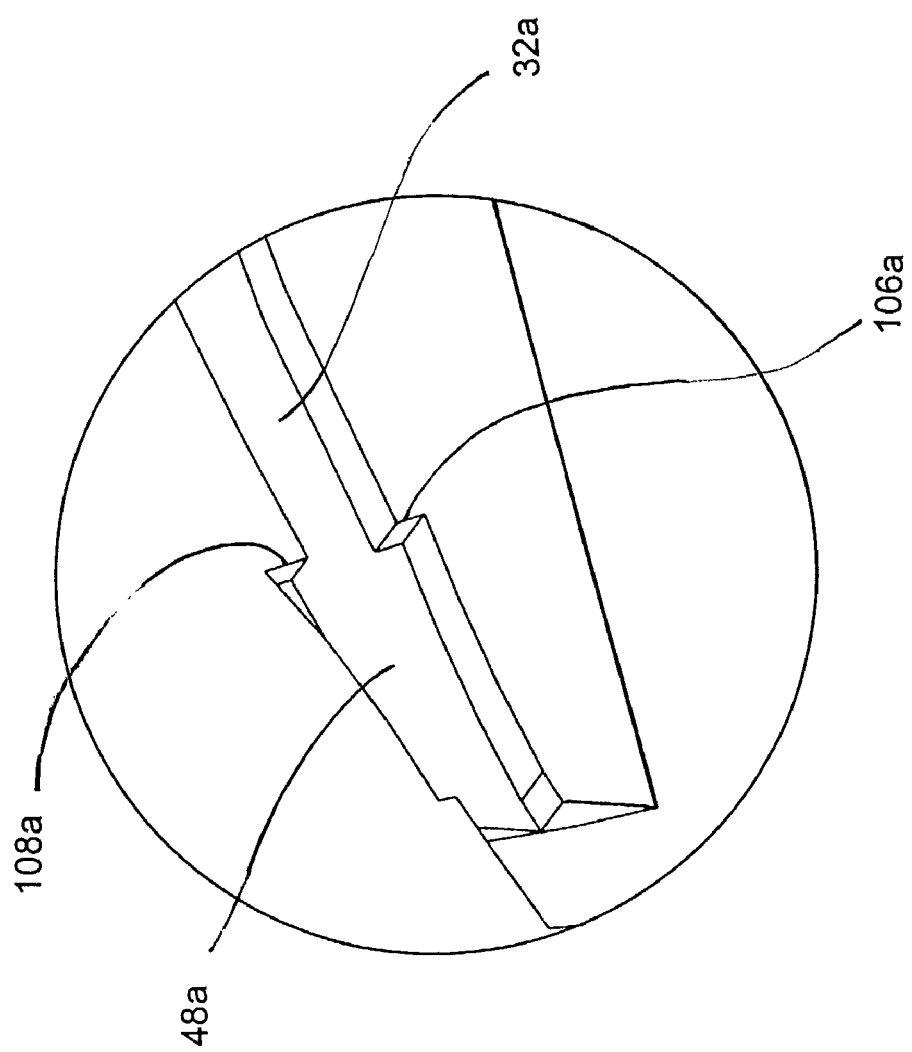
FIG. 11 is an enlarged view of the rearward portion of the guide channel from the alternate embodiment of FIG. 10.

FIGS. 9–11 depict an alternate embodiment for providing locking engagement for a needle assembly of the present invention, in which one or both of the fins include at least one, and preferably two, extensions extending from the fin. For example, a pair of fin fingers 102a, 104a may extend from opposing sides of fin 72a. Fin fingers 102a and 104a are resiliently flexible members which can be biased and flexed inwardly toward fin 72a, and which can resiliently extend outwardly in a resting state. Desirably, fin fingers 102a, 104a are flexed inwardly and are retained within guide channel 32a when the retraction assembly is in the first position, and during retraction to the second position. Guide channel 32a further includes a pair of notches 106a, 108a at the rearward end thereof, forming notch pocket 48a. Upon movement of fin fingers 102a, 104a through guide channel 32a and over notches 106a, 108a, respectively, fin fingers 102a, 104a flex outwardly due to their resilient nature, thereby expanding within notch pocket 48a. When flexed and expanded as such, the retraction assembly cannot be moved in the reverse direction due to the interference engagement of fin fingers 102a, 104a against notches 106a, 108a, thereby preventing reverse movement and re-exposure of the needle. Desirably, the force applied against the internal surface of guide channel 32a through the flexing of fin fingers 102a and 104a is less than the force exerted through the spring, such that retraction assembly 60a retracts from the first position to the second position without restriction from the flexing force of fin fingers 102a, 104a against guide channel 32a.

It is also contemplated that one or both of the fins of the retraction assembly may include only one of the fin fingers as discussed, and that the corresponding guide channels may include only a single corresponding notch for interengagement with the fin finger.

Figure 12:
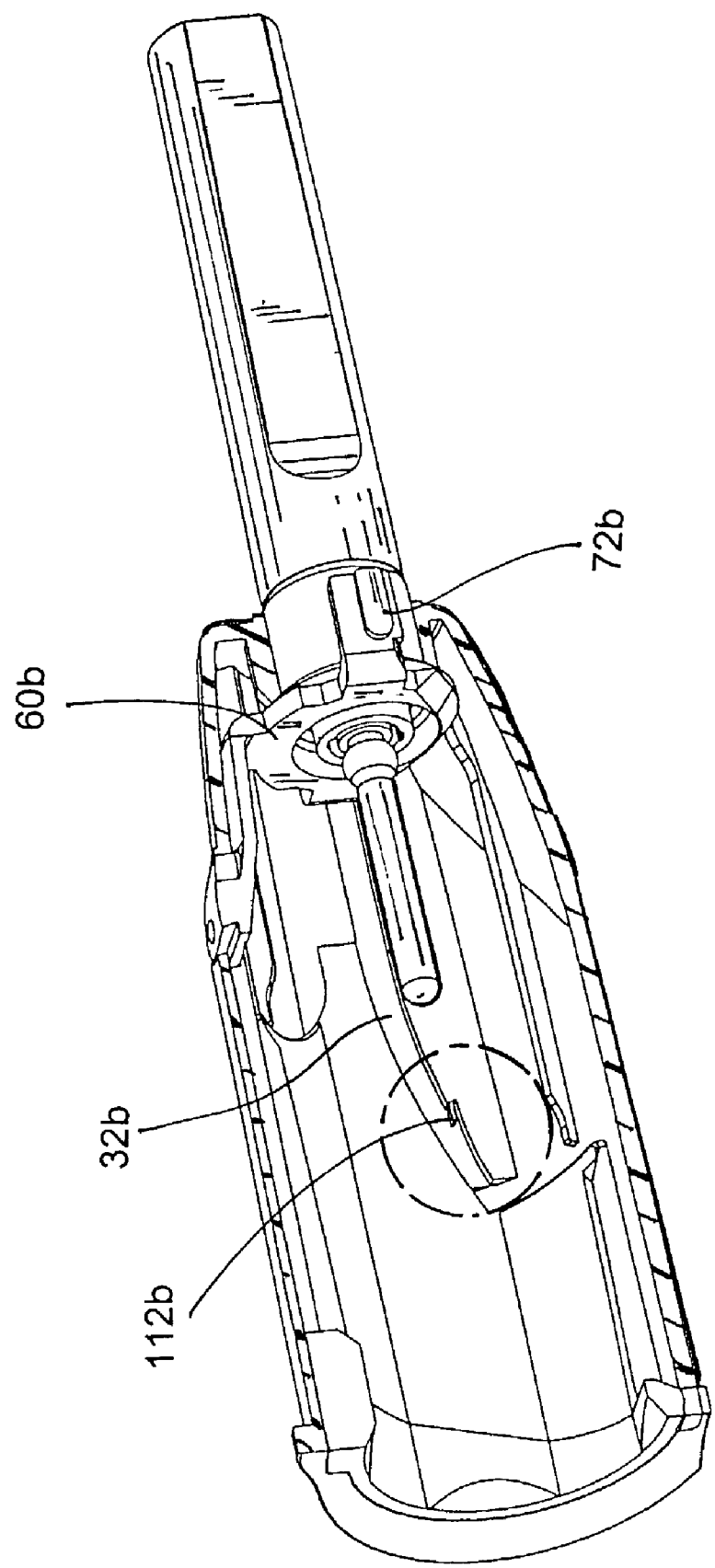
FIG. 12 is a perspective partial sectional view of a safety needle assembly in a further alternate embodiment.
Figure 13:
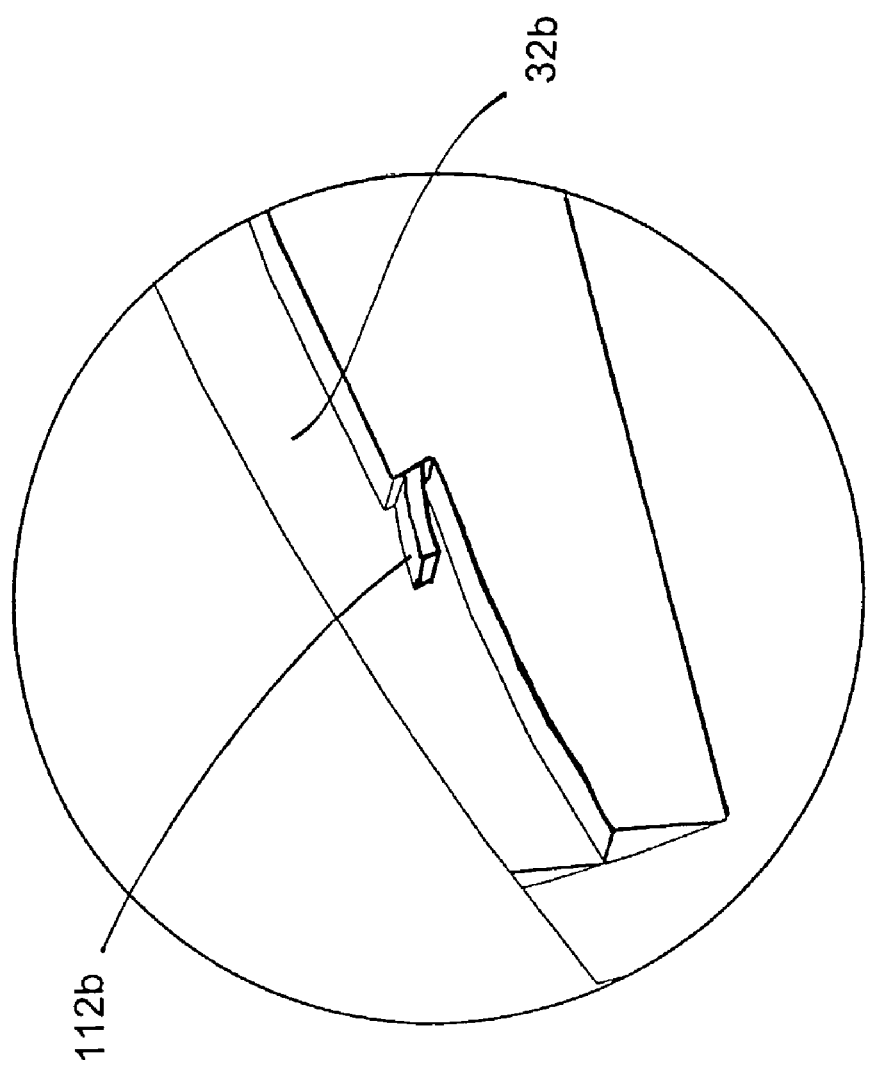
FIG. 13 is an enlarged view of the rearward portion of the guide channel from the alternate embodiment of FIG. 12.

It is further contemplated that the positioning of the fin fingers and the notches may be reversed, such that one or both of the guide channels may include an extension in the form of such a finger, which finger is capable of interference engagement with the fin as it passes into the notch pocket. For example, as shown in FIGS. 12–13, guide channel 32b may include one or more channel fingers 112b extending within guide channel 32b. Such channel finger 112b works in a similar manner as fin fingers 102a and 104a, in that it is resiliently flexible. As such, when fin 72b passes over channel finger 112b, channel finger 112b flexes, and then resumes its original position. At this point, fin 72b is moved to the rearward portion of guide channel 32b, with retraction assembly 60b being in the fully retracted position. An interference engagement is established between fin 72b and channel finger 112b, preventing reverse movement and re-exposure of the needle.

Figure 14:
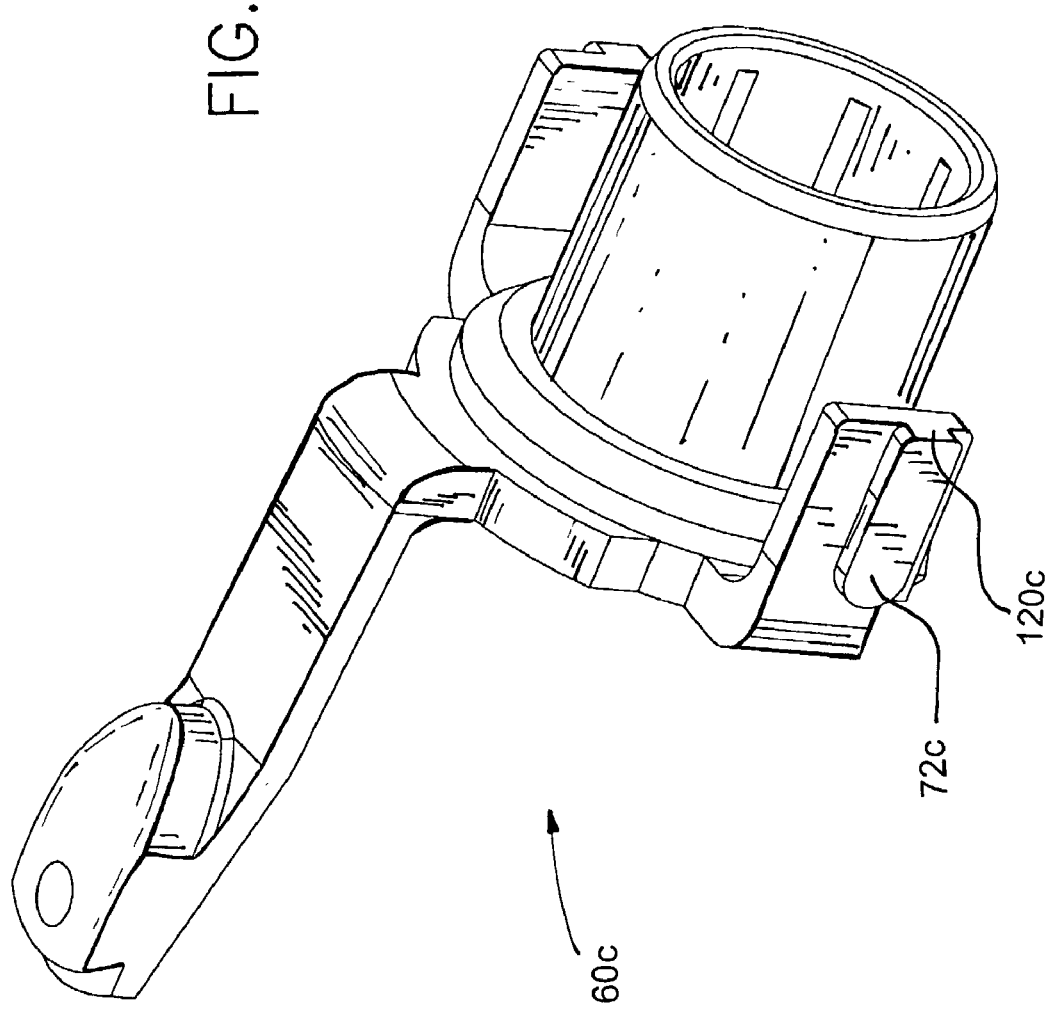
FIG. 14 is a perspective view of a retraction assembly in a further embodiment of the present invention.
Figure 15:
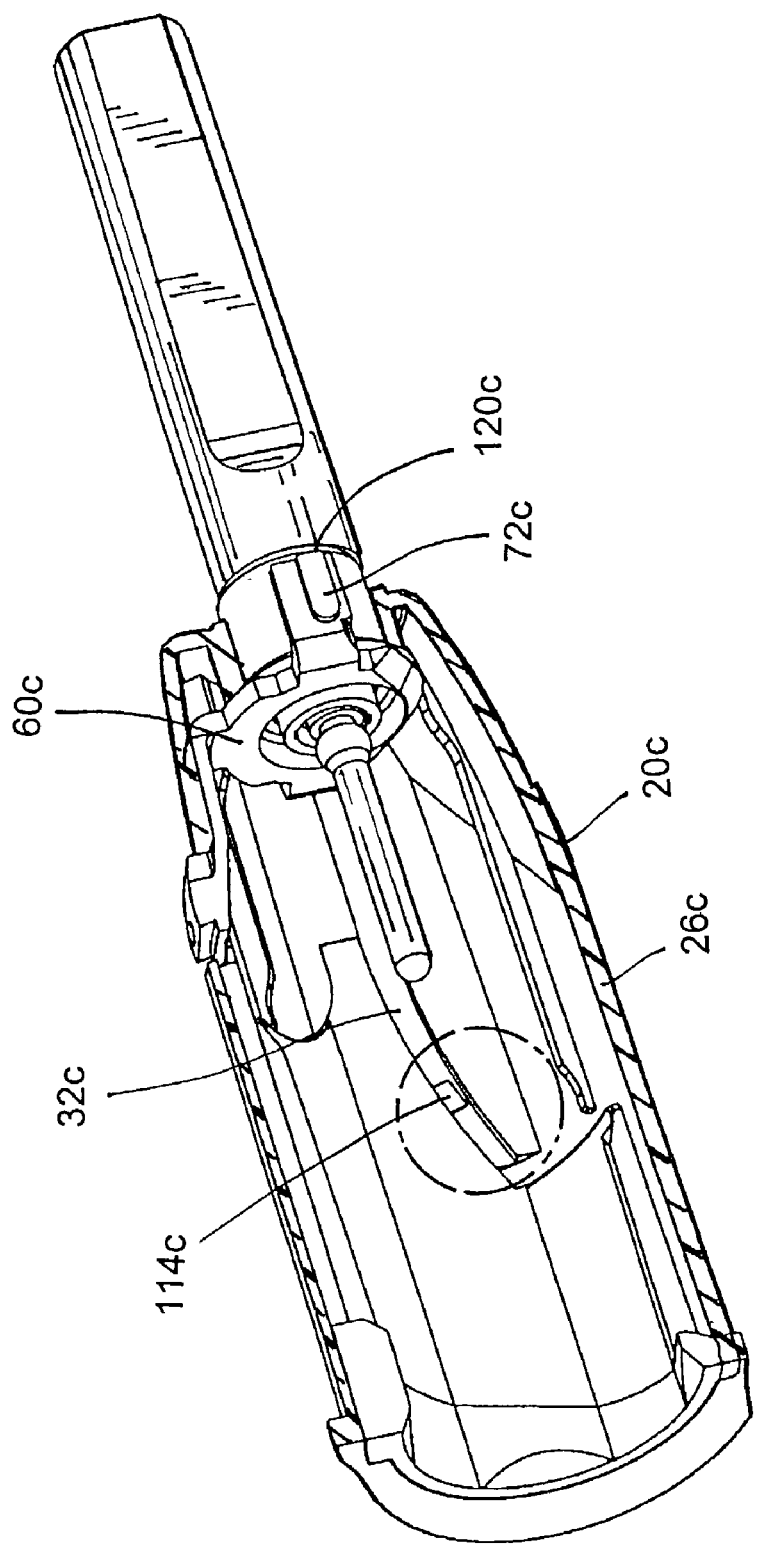
FIG. 15 is a perspective partial sectional view of a safety needle assembly in an alternate embodiment including the retraction assembly shown in FIG. 14.
Figure 16:
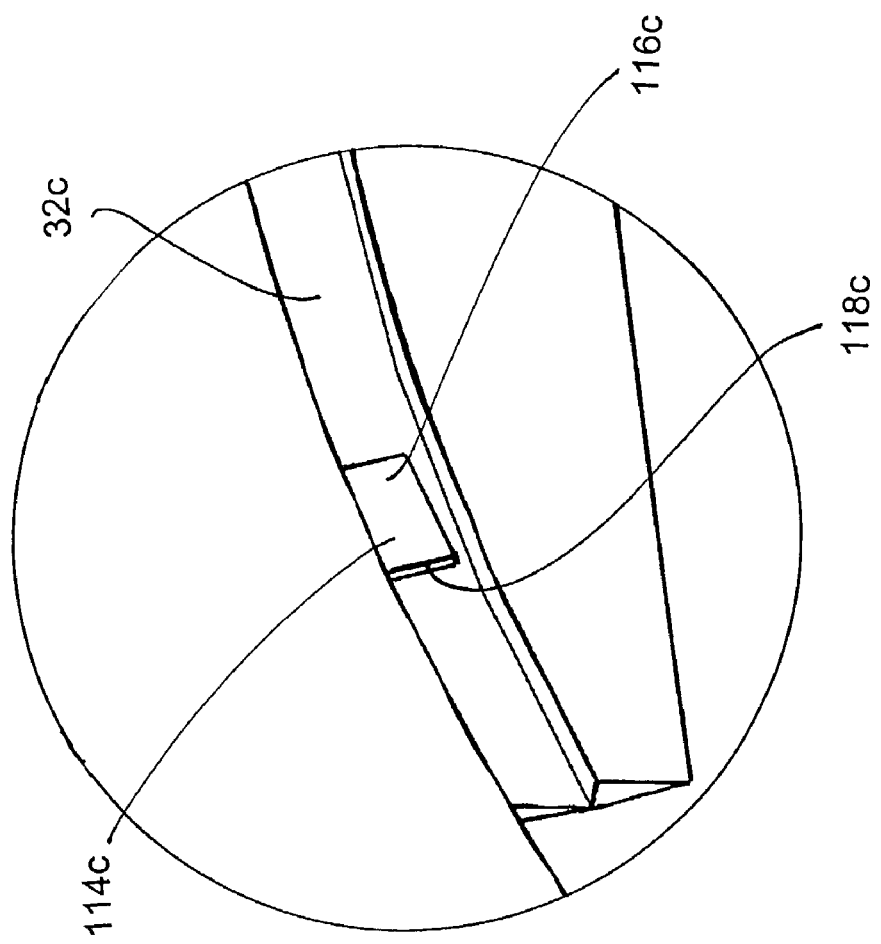
FIG. 16 is an enlarged view of the rearward portion of the guide channel from the alternate embodiment of FIG. 15.

FIGS. 14–16 depict yet a further embodiment for locking engagement of the needle assembly of the present invention, in which one or both of the guide channels include structure for providing a mechanical locking mechanism for maintaining the retraction assembly in the retracted position. In particular, guide channel 32c may include a stop 114c extending radially from an inward portion of tubular wall 26c of outer body 20c adjacent the rearward end of guide channel 32c. As such, stop 114c is generally in the form of a bump on the inner surface of tubular wall 26c within guide channel 32c. Stop 114c may be any shape or configuration, and desirably includes a tapered or ramped surface 116c at the forward face of stop 114c, and a shoulder 118c at the rearward face of stop 114c. With such a configuration, fin 72c can flex inwardly while it passes over ramped surface 116c of stop 114c during movement of retraction assembly 60c from the first position to the second position, and can flex outwardly when it passes beyond stop 114c. In such an embodiment, fin 72c desirably includes a generally planar edge surface 120c on the forward edge thereof. As such, edge surface 120c of fin 72c provides for interference engagement with shoulder 118c once fin 72c passes beyond stop 114c, thereby preventing a reverse movement of fin 72c within guide channel 32c and preventing moving of retraction assembly 60c from the second position to the first position after retraction thereof.

Figure 17:
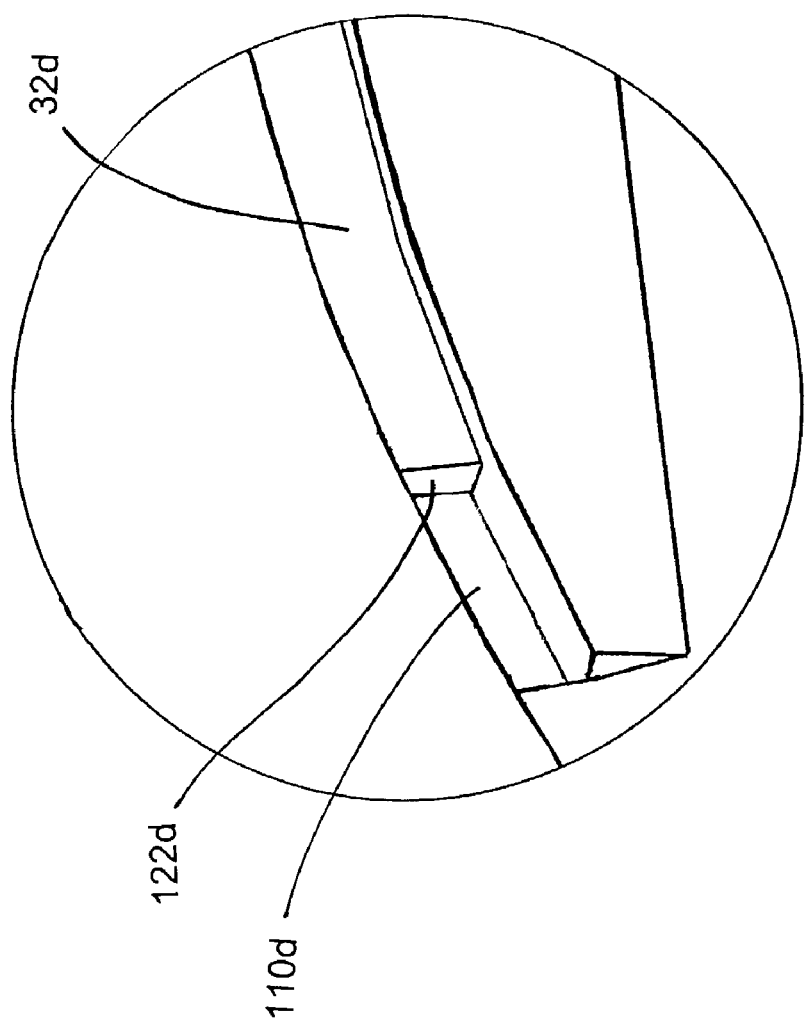
FIG. 17 is an enlarged view of the rearward portion of a guide channel in yet a further alternate embodiment.

FIG. 17 depicts yet a further embodiment for locking engagement of the needle assembly of the present invention, in which one or both of the guide channels include structure for providing a mechanical locking mechanism for maintaining the retraction assembly in the retracted position in the form of a recess pocket within the tubular wall at the rearward end of the guide channel. In particular, as shown in FIG. 17, guide channel 32d may include a radially extending outward recess 110d at the end of guide channel 32d. Outward recess 110d is provided for accommodating a fin, such as fin 72c described above, when the retraction assembly is retracted to the second position. To assist in forcing such a fin into such outward recess 110d, the fin may be slightly flexed inwardly during retraction and may possess a potential spring energy and ability to extend outward radially in order to engage such outward recess 110d. Such outward recess 110d may extend all the way through the tubular wall of the outer body to form openings which extend through the wall at the end of guide channel 32d. When the outward recesses extend all the way through the outer tubular wall, the fin can extend through such an opening upon movement of the retraction assembly from the first position to the second position. In either case, the front edge surface of the fin, such as edge surface 120c of fin 72c discussed above, extends into outward recess 110d or through the opening through the tubular wall, and is in interference engagement with wall edge 122d within outward recess 110d or through the openings extending through the tubular wall, therefore preventing movement of the retraction assembly. Thus, the retraction assembly is prevented from reversibly moving from the second position to the first position after retraction thereof.

As noted, while FIG. 17 depicts such an outward recess in only one of the guide channels, both guide channels may include such an outward recess. Moreover, such outward recesses may be provided as a locking mechanism either in addition to, or instead of any locking mechanisms for retaining the retraction assembly in the retracted position. For example, such outward recesses may be provided in one or both guide channels in combination with the locking mechanism provided by the interengagement between fins 72, 74 and notches 44, 46 discussed in connection with FIGS. 1–8.

It is further contemplated that the fin may include a radially extending finger which extends outwardly from the surface of the fin. Such a radially extending finger can engage with the stop 114c of FIGS. 14–16 to provide an interference engagement therebetween, or can radially extend within outer recess 110d of FIG. 17, thereby providing an interference engagement with wall edge 122d. As such, movement of the retraction assembly in the reverse direction is prevented.

The retracting needle assembly of the present invention may be comprised of moldable parts which can be mass produced from a variety of materials including, for example, polyethylene, polyvinyl chloride, polystyrene, or the like. Materials will be selected which will provide the proper support for the structure of the invention in its use, but which will also provide a degree of resiliency for the purpose of providing the cooperative relative movement.

While the needle assembly of the present invention has been described in terms of one embodiment for use in connection with a blood collection system, it is further contemplated that the needle assembly could be used with other medical procedures, such as in conjunction with a conventional intravenous infusion set, as are well-known in the art for use with conventional needle assemblies.

What is claimed is:

1. A retractable safety needle assembly comprising:
    a) a generally tubular outer body including a first end, a second end and a tubular wall extending along an axis from said first end to said second end to define an interior opening within said outer body, said outer body including a guide channel at least a portion of which is offset from said axis;
    b) a retraction assembly positioned within said interior opening of said outer body, said retraction assembly including a cannula having an intravenous puncture tip and a non-patient puncture tip and including a fin for corresponding engagement with said guide channel of said outer body, said retraction assembly adapted for movement within said interior opening of said outer body from a first position in which said intravenous puncture tip extends from said first end of said outer body to a second position in which said intravenous puncture tip and said non-patient puncture tip are contained entirely within said outer body and said cannula is offset from said axis of said outer body;
    c) a retaining element for preventing movement of said retraction assembly between said first position and said second position;
    d) a biasing element for applying a retraction force between said retraction assembly and said outer body to move said retraction assembly from said first position to said second position upon release of said retaining element; and
    e) a lock mechanism for locking said retraction assembly in said second position, wherein said guide channel includes a notch,
wherein said notch forms a notch pocket located at an end of the guide channel, said guide channel end being located at said portion that is offset from said axis, and wherein said notch acts as the lock mechanism for preventing said fin from moving within said guide channel and thereby preventing said retraction assembly from moving from said second position to said first position.

2. The needle assembly as in claim 1, wherein said biasing element comprises a compression spring.

3. The needle assembly as in claim 1, wherein said tubular wall of said outer body includes a recess extending within the interior opening of said outer body adapted for accommodating said non-patient puncture tip when said retraction assembly is in said second position.

4. The needle assembly as in claim 1, wherein said outer body includes an opening extending through said tubular wall and said retraction assembly includes a tab extending through said opening, said retaining element comprising an interference engagement between said tab and said tubular wall.

5. The needle assembly as in claim 1, wherein said retraction assembly is irreversibly movable from said first position to said second position.

6. The needle assembly as in claim 1, wherein attempted movement of said retraction assembly from said second position to said first position causes said intravenous puncture tip to contact an interior portion of said tubular outer body at said first end, thereby preventing said retraction assembly from moving from said second position to said first position.

7. The needle assembly as in claim 1, wherein attempted movement of said retraction assembly from said second position to said first position causes either said intravenous puncture tip to contact an interior portion of said tubular outer body at said first end, or said fin to contact said notch, thereby preventing said retraction assembly from moving from said second position to said first position.

8. The needle assembly as in claim 1, wherein said outer body includes a pair of guide channels on opposing sides of said tubular wall and said retraction assembly includes a pair of fins for respective corresponding engagement with said pair of guide channels.

9. The needle assembly as in claim 8, wherein said pair of guide channels extend along opposing sides of said tubular wall and slope downwardly toward said second end of said outer body.

10. The needle assembly as in claim 1, further comprising an elastomeric sleeve extending about said non-patient puncture tip.

11. The needle assembly as in claim 1, further comprising a needle cover extending about said intravenous puncture tip.

12. A retractable safety needle assembly comprising:
 a) a generally tubular outer body including a first end, a second end and a tubular wall extending along an axis from said first end to said second end to define an interior opening within said outer body, said outer body including a guide channel at least a portion of which is offset from said axis;
 b) an insert extending within said second end of said outer body, said insert providing structure forming at least a portion of said guide channel;
 c) a retraction assembly positioned within said interior opening of said outer body, said retraction assembly including a cannula having an intravenous puncture tip and a non-patient puncture tip and including a fin for corresponding engagement with said guide channel of said outer body, said retraction assembly adapted for movement within said interior opening of said outer body from a first position in which said intravenous puncture tip extends from said first end of said outer body to a second position in which said intravenous puncture tip and said non-patient puncture tip are contained entirely within said outer body and said cannula is offset from said axis of said outer body;
 d) a retaining element for preventing movement of said retraction assembly between said first position and said second position;
 e) a biasing element for applying a retraction force between said retraction assembly and said outer body to move said retraction assembly from said first position to said second position upon release of said retaining element; and
 f) a lock mechanism for locking said retraction assembly in said second position, wherein said guide channel includes a notch,
 wherein said notch forms a notch pocket located at an end of the guide channel, said guide channel end being located at said portion that is offset from said axis, and
 wherein said notch acts as the lock mechanism for preventing said fin from moving within said guide channel and thereby preventing said retraction assembly from moving from said second position to said first position.

13. The needle assembly as in claim 12, wherein said tubular wall of said outer body includes a recess extending within the interior opening of said outer body adapted for accommodating said non-patient puncture tip when said retraction assembly is in said second position, wherein said recess comprises structure established through engagement between said outer body and said insert extending within said second end of said outer body.

14. The needle assembly as in claim 12, wherein said outer body includes an opening extending through said tubular wall and said retraction assembly includes a tab extending through said opening, said retaining element comprising an interference engagement between said tab and said tubular wall.

15. The needle assembly as in claim 14, further comprising a channel extending from said opening toward said second end of said outer body for slidable engagement of said tab therein, wherein said channel is formed in said insert and is established within said outer body through engagement between said outer body and said insert extending within said second end of said outer body.

16. The needle assembly as in claim 12, wherein said biasing element comprises a compression spring.

17. The needle assembly as in claim 12, wherein said retraction assembly is irreversibly movable from said first position to said second position.

18. The needle assembly as in claim 12, wherein attempted movement of said retraction assembly from said second position to said first position causes said intravenous puncture tip to contact an interior portion of said tubular outer body at said first end, thereby preventing said retraction assembly from moving from said second position to said first position.

19. The needle assembly as in claim 12, wherein attempted movement of said retraction assembly from said second position to said first position causes either said intravenous puncture tip to contact an interior portion of said tubular outer body at said first end, or said fin to contact said notch, thereby preventing said retraction assembly from moving from said second position to said first position.

20. The needle assembly as in claim 12, wherein said outer body includes a pair of guide channels on opposing sides of said tubular wall, said insert providing structure forming at least a portion of said pair of guide channels, and said retraction assembly includes a pair of fins for respective corresponding engagement with said pair of guide channels.

21. The needle assembly as in claim 20, wherein said pair of guide channels extend along opposing sides of said tubular wall at said insert and slope downwardly toward said second end of said outer body.

22. The needle assembly as in claim 12, wherein a portion of said guide channel adjacent said first end of said outer body extends generally parallel to said axis and a portion of said guide channel formed by said insert is offset from said axis.

23. The needle assembly as in claim 1, wherein a portion of said guide channel adjacent said first end of said outer body extends generally parallel to said axis and a portion of said guide channel extending toward said second end of said outer body is offset from said axis.

24. The needle assembly as in claim 12, wherein a portion of said guide channel adjacent said first end of said outer body extends generally parallel to said axis and a portion of said guide channel extending toward said second end of said outer body is offset from said axis.

* * * * *